US012440634B2

(12) United States Patent
Cipollone et al.

(10) Patent No.: US 12,440,634 B2
(45) Date of Patent: Oct. 14, 2025

(54) VENTILATOR SYSTEMS WITH INTEGRATED OXYGEN DELIVERY, AND ASSOCIATED DEVICES AND METHODS

(71) Applicant: Ventec Life Systems, Inc., Bothell, WA (US)

(72) Inventors: Joseph Cipollone, Bothell, WA (US); Andrew R. Chapman, Bothell, WA (US); Luke Kobler Johnson, Seattle, WA (US); Samir S. Ahmad, San Diego, CA (US); Michael B. Holmes, Bothell, WA (US); Christopher T. Kiple, Seattle, WA (US)

(73) Assignee: Ventec Life Systems, Inc., Bothell, WA (US)

( * ) Notice: Subject to any disclaimer, the term of this patent is extended or adjusted under 35 U.S.C. 154(b) by 675 days.

(21) Appl. No.: 17/558,363

(22) Filed: Dec. 21, 2021

(65) Prior Publication Data

US 2022/0193354 A1 Jun. 23, 2022

Related U.S. Application Data

(60) Provisional application No. 63/128,739, filed on Dec. 21, 2020.

(51) Int. Cl.

*A61M 16/00* (2006.01)
*A61M 16/06* (2006.01)
*A61M 16/20* (2006.01)

(52) U.S. Cl.

CPC ...... *A61M 16/026* (2017.08); *A61M 16/0003* (2014.02); *A61M 16/0672* (2014.02);
(Continued)

(58) Field of Classification Search

None
See application file for complete search history.

(56) References Cited

U.S. PATENT DOCUMENTS 3,191,596 A 6/1965 Bird
3,234,932 A 2/1966 Bird
(Continued)

FOREIGN PATENT DOCUMENTS

CN 87206076 U 4/1988
CN 2718262 Y 8/2005
(Continued)

OTHER PUBLICATIONS

US 8,012,240 B2, 09/2011, Sprinkle (withdrawn)
(Continued)

*Primary Examiner* — Latoya M Louis
(74) *Attorney, Agent, or Firm* — Perkins Coie LLP

(57) ABSTRACT

The present technology is directed to ventilator systems that can provide both ventilation therapy and oxygen therapy. The systems described herein may include a ventilation assembly that can provide inspiratory gas to a patient circuit and an oxygen assembly that can provide pulses of oxygen to an oxygen delivery circuit. In some embodiments, the oxygen delivery circuit is distinct from the patient circuit. For example, the patient circuit can include a corrugated conduit coupled a ventilation mask, and the oxygen delivery circuit can include a nasal cannula. The ventilation mask can be positioned over the nasal cannula so that the patient can receive both the inspiratory gases and the pulses of oxygen.

16 Claims, 11 Drawing Sheets

(52) U.S. Cl.
CPC ... *A61M 16/209* (2014.02); *A61M 2016/0027* (2013.01); *A61M 2202/0208* (2013.01)

(56) References Cited

U.S. PATENT DOCUMENTS 3,789,837 A 2/1974 Philips et al.
3,806,102 A 4/1974 Valenta et al.
3,875,626 A 4/1975 Tysk et al.
3,993,059 A 11/1976 Sjostrand
4,280,399 A 7/1981 Cunning
4,331,455 A 5/1982 Sato
4,357,936 A 11/1982 Ellestad et al.
4,367,767 A 1/1983 Hurd
4,386,945 A 6/1983 Gardner
4,401,116 A 8/1983 Fry et al.
4,417,573 A 11/1983 De Vries
4,425,914 A 1/1984 Ray et al.
4,449,990 A 5/1984 Tedford, Jr.
4,450,838 A 5/1984 Miodownik
4,459,982 A 7/1984 Fry
4,502,481 A 3/1985 Christian
4,502,873 A 3/1985 Mottram et al.
4,516,424 A 5/1985 Rowland
4,527,557 A 7/1985 Devries et al.
4,545,790 A 10/1985 Miller et al.
4,561,287 A 12/1985 Rowland
4,576,616 A 3/1986 Mottram et al.
4,602,653 A 7/1986 Ruiz-vela et al.
4,621,632 A 11/1986 Bartels et al.
4,627,860 A 12/1986 Rowland
4,637,386 A 1/1987 Baum
4,648,395 A 3/1987 Sato et al.
4,648,888 A 3/1987 Rowland
4,681,099 A 7/1987 Sato et al.
4,682,591 A 7/1987 Jones
4,702,240 A 10/1987 Chaoui
4,794,922 A 1/1989 Devries
4,807,616 A 2/1989 Adahan
4,813,979 A 3/1989 Miller et al.
4,869,733 A 9/1989 Stanford
4,880,443 A 11/1989 Miller et al.
4,905,685 A 3/1990 Olsson et al.
4,936,297 A 6/1990 Greiff et al.
4,941,469 A 7/1990 Adahan
4,971,609 A 11/1990 Pawlos
4,983,190 A 1/1991 Verrando et al.
4,993,269 A 2/1991 Guillaume et al.
5,002,591 A 3/1991 Stanford
5,014,694 A 5/1991 Devries
5,021,137 A 6/1991 Joshi et al.
5,024,219 A 6/1991 Dietz
5,034,023 A 7/1991 Thompson
5,071,453 A 12/1991 Hradek et al.
5,072,729 A 12/1991 Devries
5,101,656 A 4/1992 Miller
5,107,831 A 4/1992 Halpern et al.
5,127,400 A 7/1992 Devries et al.
5,129,924 A 7/1992 Schultz
5,134,329 A 7/1992 Lang
5,161,525 A 11/1992 Kimm et al.
5,166,563 A 11/1992 Bassine
5,169,506 A 12/1992 Michaels
5,186,793 A 2/1993 Michaels
5,265,594 A 11/1993 Olsson et al.
5,273,031 A 12/1993 Olsson et al.
5,275,642 A 1/1994 Bassine
5,296,110 A 3/1994 Tabatabaie-raissi
5,331,995 A 7/1994 Westfall et al.
5,335,426 A 8/1994 Settlemyer et al.
5,354,361 A 10/1994 Coffield
5,370,112 A 12/1994 Perkins
5,378,345 A 1/1995 Taylor et al.
5,397,443 A 3/1995 Michaels
5,400,777 A 3/1995 Olsson et al.
5,469,372 A 11/1995 Mcbrearty et al.
5,474,062 A 12/1995 Devires et al.
5,474,595 A 12/1995 Mccombs
5,494,028 A 2/1996 Devries et al.
5,497,767 A 3/1996 Olsson et al.
5,501,212 A 3/1996 Psaros
5,540,220 A 7/1996 Gropper et al.
5,540,233 A 7/1996 Larsson et al.
5,575,283 A 11/1996 Sjoestrand
5,578,115 A 11/1996 Cole
5,676,133 A 10/1997 Hickle et al.
5,694,924 A 12/1997 Cewers
5,694,926 A 12/1997 Devries et al.
5,701,883 A 12/1997 Hete et al.
5,706,801 A 1/1998 Remes et al.
5,720,277 A 2/1998 Olsson et al.
5,740,796 A 4/1998 Skog
5,743,253 A 4/1998 Castor et al.
5,746,806 A 5/1998 Aylsworth et al.
5,765,557 A 6/1998 Warters
5,765,558 A 6/1998 Psaros et al.
5,766,310 A 6/1998 Cramer
5,810,324 A 9/1998 Eriksson et al.
5,827,358 A 10/1998 Kulish et al.
5,845,633 A 12/1998 Psaros
5,849,219 A 12/1998 De Laat et al.
5,858,062 A 1/1999 Mcculloh et al.
5,858,063 A 1/1999 Cao et al.
5,862,802 A 1/1999 Bird
5,868,133 A 2/1999 Devries et al.
5,871,564 A 2/1999 Mccombs
5,875,777 A 3/1999 Eriksson
5,878,744 A 3/1999 Pfeiffer
5,881,722 A 3/1999 Devries et al.
5,893,944 A 4/1999 Dong
5,896,857 A 4/1999 Hely et al.
5,906,672 A 5/1999 Michaels et al.
5,917,135 A 6/1999 Michaels et al.
5,931,162 A 8/1999 Christian
5,937,853 A 8/1999 Stroem
5,948,142 A 9/1999 Holmes et al.
5,957,130 A 9/1999 Krahbichler et al.
5,968,236 A 10/1999 Bassine
5,988,165 A 11/1999 Richey, II et al.
5,997,617 A 12/1999 Czabala et al.
6,010,555 A 1/2000 Smolarek et al.
6,035,851 A 3/2000 Wallen
6,062,218 A 5/2000 Krahbichler et al.
6,068,680 A 5/2000 Kulish et al.
6,073,630 A 6/2000 Adahan
6,095,139 A 8/2000 Psaros
6,102,038 A 8/2000 Devries
6,112,744 A 9/2000 Hoegnelid
6,113,673 A 9/2000 Loutfy et al.
6,123,074 A 9/2000 Hete et al.
6,152,132 A 11/2000 Psaros
6,152,134 A 11/2000 Webber et al.
6,152,135 A 11/2000 Devries et al.
6,155,252 A 12/2000 Warters
6,156,100 A 12/2000 Conrad et al.
6,158,430 A 12/2000 Pfeiffer et al.
6,162,283 A 12/2000 Conrad et al.
6,176,897 B1 1/2001 Keefer
6,186,142 B1 2/2001 Schmidt et al.
6,189,532 B1 2/2001 Hely et al.
6,190,441 B1 2/2001 Czabala et al.
6,192,885 B1 2/2001 Jalde
6,217,635 B1 4/2001 Conrad et al.
6,234,170 B1 5/2001 Bergkvist
6,253,767 B1 7/2001 Mantz
6,263,873 B1 7/2001 Hedenberg
6,269,811 B1 8/2001 Duff
6,298,848 B1 10/2001 Skog
6,302,107 B1 10/2001 Richey, II et al.
6,344,069 B2 2/2002 Smolarek et al.
6,346,139 B1 2/2002 Czabala
6,348,082 B1 2/2002 Murdoch et al.
6,360,740 B1 3/2002 Ward et al.
6,386,235 B1 5/2002 Mcculloh et al.
6,393,802 B1 5/2002 Bowser et al.

(56) References Cited

U.S. PATENT DOCUMENTS

| | | | |
|---|---|---|---|
| 6,394,089 | B1 | 5/2002 | Cantrill et al. |
| 6,395,065 | B1 | 5/2002 | Murdoch et al. |
| 6,412,483 | B1 | 7/2002 | Jones et al. |
| 6,446,630 | B1 | 9/2002 | Todd, Jr. |
| 6,471,744 | B1 | 10/2002 | Hill |
| 6,478,850 | B2 | 11/2002 | Warren |
| 6,478,857 | B2 | 11/2002 | Czabala |
| 6,497,755 | B2 | 12/2002 | Murdoch et al. |
| 6,514,318 | B2 | 2/2003 | Keefer |
| 6,514,319 | B2 | 2/2003 | Keefer et al. |
| 6,516,798 | B1 | 2/2003 | Davies |
| 6,520,176 | B1 | 2/2003 | Dubois et al. |
| 6,524,370 | B2 | 2/2003 | Maheshwary et al. |
| 6,526,970 | B2 | 3/2003 | Devries et al. |
| 6,532,956 | B2 | 3/2003 | Hill |
| 6,547,851 | B2 | 4/2003 | Warren |
| 6,551,384 | B1 | 4/2003 | Ackley et al. |
| 6,553,992 | B1 | 4/2003 | Berthon-jones et al. |
| 6,558,451 | B2 | 5/2003 | Mccombs et al. |
| 6,564,798 | B1 | 5/2003 | Jalde |
| 6,565,635 | B2 | 5/2003 | Keefer et al. |
| 6,581,594 | B1 | 6/2003 | Drew et al. |
| 6,595,213 | B2 | 7/2003 | Bennarsten |
| 6,601,583 | B2 | 8/2003 | Pessala et al. |
| 6,622,726 | B1 | 9/2003 | Du |
| 6,626,175 | B2 | 9/2003 | Jafari et al. |
| 6,629,525 | B2 | 10/2003 | Hill et al. |
| 6,640,807 | B2 | 11/2003 | Bennarsten |
| 6,641,644 | B2 | 11/2003 | Jagger et al. |
| 6,641,645 | B1 | 11/2003 | Lee et al. |
| 6,644,312 | B2 | 11/2003 | Berthon-jones et al. |
| 6,651,652 | B1 | 11/2003 | Waard |
| 6,651,658 | B1 | 11/2003 | Hill et al. |
| 6,651,692 | B2 | 11/2003 | Meckes et al. |
| 6,660,065 | B2 | 12/2003 | Byrd et al. |
| 6,668,828 | B1 | 12/2003 | Figley et al. |
| 6,679,258 | B1 | 1/2004 | Stroem |
| 6,691,702 | B2 | 2/2004 | Appel et al. |
| 6,694,978 | B1 | 2/2004 | Bennarsten |
| 6,702,880 | B2 | 3/2004 | Roberts et al. |
| 6,712,876 | B2 | 3/2004 | Cao et al. |
| 6,712,877 | B2 | 3/2004 | Cao et al. |
| 6,739,334 | B2 | 5/2004 | Valeij |
| 6,740,146 | B2 | 5/2004 | Simonds |
| 6,755,193 | B2 | 6/2004 | Berthon-jones et al. |
| 6,758,216 | B1 | 7/2004 | Berthon-jones et al. |
| 6,761,166 | B2 | 7/2004 | Ahlmen et al. |
| 6,764,534 | B2 | 7/2004 | Mccombs et al. |
| 6,782,888 | B1 | 8/2004 | Friberg et al. |
| 6,793,719 | B2 | 9/2004 | Kim et al. |
| 6,805,122 | B2 | 10/2004 | Richey, II et al. |
| 6,811,590 | B2 | 11/2004 | Lee et al. |
| 6,837,244 | B2 | 1/2005 | Yagi et al. |
| 6,845,773 | B2 | 1/2005 | Berthon-jones et al. |
| 6,860,858 | B2 | 3/2005 | Green et al. |
| 6,863,068 | B2 | 3/2005 | Jamison et al. |
| 6,866,700 | B2 | 3/2005 | Amann |
| 6,877,511 | B2 | 4/2005 | Devries et al. |
| 6,889,726 | B2 | 5/2005 | Richey, II et al. |
| 6,896,721 | B1 | 5/2005 | Lynn |
| 6,908,503 | B2 | 6/2005 | Mccombs et al. |
| 6,910,480 | B1 | 6/2005 | Berthon-jones |
| 6,923,180 | B2 | 8/2005 | Richey, II et al. |
| 6,935,460 | B2 | 8/2005 | Mccombs et al. |
| 6,949,133 | B2 | 9/2005 | Mccombs et al. |
| 6,997,881 | B2 | 2/2006 | Green et al. |
| 7,000,610 | B2 | 2/2006 | Bennarsten et al. |
| 7,032,592 | B2 | 4/2006 | Castor et al. |
| 7,040,318 | B2 | 5/2006 | Daescher et al. |
| 7,055,522 | B2 | 6/2006 | Berthon-jones |
| 7,066,985 | B2 | 6/2006 | Deane et al. |
| 7,077,133 | B2 | 7/2006 | Yagi et al. |
| 7,081,745 | B2 | 7/2006 | Haveri |
| 7,089,937 | B2 | 8/2006 | Berthon-jones et al. |
| 7,094,275 | B2 | 8/2006 | Keefer et al. |
| 7,096,866 | B2 | 8/2006 | Be'eri et al. |
| 7,100,609 | B2 | 9/2006 | Berthon-jones et al. |
| 7,105,038 | B2 | 9/2006 | Lee et al. |
| 7,121,276 | B2 | 10/2006 | Jagger et al. |
| 7,121,277 | B2 | 10/2006 | Stroem |
| 7,135,059 | B2 | 11/2006 | Deane et al. |
| 7,156,903 | B2 | 1/2007 | Mccombs |
| 7,171,963 | B2 | 2/2007 | Jagger et al. |
| 7,179,326 | B2 | 2/2007 | Nakamura et al. |
| 7,188,621 | B2 | 3/2007 | DeVries et al. |
| 7,213,468 | B2 | 5/2007 | Fujimoto |
| 7,219,666 | B2 | 5/2007 | Friberg et al. |
| 7,222,623 | B2 | 5/2007 | Devries et al. |
| 7,250,073 | B2 | 7/2007 | Keefer et al. |
| 7,255,103 | B2 | 8/2007 | Bassin |
| 7,279,029 | B2 | 10/2007 | Occhialini et al. |
| 7,294,170 | B2 | 11/2007 | Richey, II et al. |
| 7,318,437 | B2 | 1/2008 | Gunaratnam et al. |
| 7,329,304 | B2 | 2/2008 | Bliss et al. |
| 7,347,207 | B2 | 3/2008 | Ahlmen et al. |
| 7,350,521 | B2 | 4/2008 | Whitley et al. |
| 7,367,337 | B2 | 5/2008 | Berthon-jones et al. |
| 7,368,005 | B2 | 5/2008 | Bliss et al. |
| RE40,402 | E | 6/2008 | Leonhardt et al. |
| 7,402,193 | B2 | 7/2008 | Bliss et al. |
| 7,406,966 | B2 | 8/2008 | Wondka |
| 7,427,315 | B2 | 9/2008 | Dolensky et al. |
| 7,428,902 | B2 | 9/2008 | Du et al. |
| 7,429,289 | B2 | 9/2008 | Dolensky et al. |
| 7,431,032 | B2 | 10/2008 | Jagger et al. |
| 7,438,745 | B2 | 10/2008 | Deane et al. |
| 7,445,546 | B2 | 11/2008 | Hondmann et al. |
| 7,445,663 | B1 | 11/2008 | Hunter et al. |
| 7,455,717 | B2 | 11/2008 | Sprinkle |
| 7,473,299 | B2 | 1/2009 | Occhialini et al. |
| 7,491,261 | B2 | 2/2009 | Warren et al. |
| 7,497,215 | B1 | 3/2009 | Nguyen et al. |
| 7,510,601 | B2 | 3/2009 | Whitley et al. |
| 7,517,385 | B2 | 4/2009 | Winter |
| 7,524,365 | B2 | 4/2009 | Lin |
| 7,527,053 | B2 | 5/2009 | Devries et al. |
| 7,533,872 | B2 | 5/2009 | Lee et al. |
| 7,550,031 | B2 | 6/2009 | Hunter et al. |
| 7,550,036 | B2 | 6/2009 | Lee et al. |
| 7,556,670 | B2 | 7/2009 | Aylsworth et al. |
| 7,559,326 | B2 | 7/2009 | Smith et al. |
| 7,585,351 | B2 | 9/2009 | Deane et al. |
| 7,590,551 | B2 | 9/2009 | Auer |
| 7,604,004 | B2 | 10/2009 | Jagger et al. |
| 7,604,005 | B2 | 10/2009 | Jagger et al. |
| 7,628,151 | B2 | 12/2009 | Bassin |
| 7,637,989 | B2 | 12/2009 | Bong |
| 7,655,059 | B2 | 2/2010 | Wang et al. |
| 7,655,063 | B2 | 2/2010 | Wang et al. |
| 7,682,428 | B2 | 3/2010 | Nawata et al. |
| 7,682,429 | B2 | 3/2010 | Dolensky et al. |
| 7,686,870 | B1 | 3/2010 | Deane et al. |
| 7,704,304 | B2 | 4/2010 | Warren et al. |
| 7,708,802 | B1 | 5/2010 | Deane et al. |
| 7,708,818 | B2 | 5/2010 | Clark |
| 7,717,981 | B2 | 5/2010 | Labuda et al. |
| 7,722,700 | B2 | 5/2010 | Sprinkle |
| 7,727,160 | B2 | 6/2010 | Green et al. |
| 7,730,887 | B2 | 6/2010 | Deane et al. |
| 7,753,996 | B1 | 7/2010 | Deane et al. |
| 7,758,672 | B2 | 7/2010 | Lee et al. |
| 7,763,103 | B2 | 7/2010 | Dolensky et al. |
| 7,766,010 | B2 | 8/2010 | Jagger et al. |
| 7,771,511 | B2 | 8/2010 | Dolensky |
| 7,780,768 | B2 | 8/2010 | Taylor et al. |
| 7,780,769 | B2 | 8/2010 | Dolensky et al. |
| 7,794,522 | B2 | 9/2010 | Bliss et al. |
| 7,828,878 | B2 | 11/2010 | Zhong et al. |
| 7,837,761 | B2 | 11/2010 | Bliss et al. |
| 7,841,343 | B2 | 11/2010 | Deane et al. |
| 7,849,854 | B2 | 12/2010 | Devries et al. |
| 7,857,894 | B2 | 12/2010 | Taylor et al. |
| 7,861,716 | B2 | 1/2011 | Borrello |
| 7,866,315 | B2 | 1/2011 | Jagger et al. |

(56) References Cited

U.S. PATENT DOCUMENTS

| | | | |
|---|---|---|---|
| 7,874,290 | B2 | 1/2011 | Chalvignac |
| 7,875,105 | B2 | 1/2011 | Chambers et al. |
| 7,892,322 | B2 | 2/2011 | Ono et al. |
| 7,909,034 | B2 | 3/2011 | Sinderby et al. |
| 7,914,459 | B2 | 3/2011 | Green et al. |
| 7,918,925 | B2 | 4/2011 | Dolensky et al. |
| 7,922,789 | B1 | 4/2011 | Deane et al. |
| 7,934,499 | B2 | 5/2011 | Berthon-jones |
| 7,954,493 | B2 | 6/2011 | Nawata |
| 8,006,692 | B2 | 8/2011 | Smith et al. |
| 8,016,916 | B2 | 9/2011 | Ono et al. |
| 8,016,918 | B2 | 9/2011 | Labuda et al. |
| 8,016,925 | B2 | 9/2011 | Mccombs et al. |
| 8,020,553 | B2 | 9/2011 | Jagger et al. |
| 8,051,852 | B2 | 11/2011 | Bassin |
| 8,062,003 | B2 | 11/2011 | Goertzen |
| 8,070,853 | B2 | 12/2011 | Sprinkle |
| 8,070,864 | B2 | 12/2011 | Uchiyama et al. |
| 8,070,922 | B2 | 12/2011 | Nelson et al. |
| 8,075,676 | B2 | 12/2011 | Thompson et al. |
| 8,100,125 | B2 | 1/2012 | Duquette et al. |
| 8,118,024 | B2 | 2/2012 | Devries et al. |
| 8,122,885 | B2 | 2/2012 | Berthon-jones et al. |
| 8,123,497 | B2 | 2/2012 | Richey, II et al. |
| 8,142,544 | B2 | 3/2012 | Taylor et al. |
| 8,146,596 | B2 | 4/2012 | Smith et al. |
| 8,147,597 | B2 | 4/2012 | Dolensky et al. |
| 8,156,937 | B2 | 4/2012 | Devries et al. |
| 8,167,988 | B2 | 5/2012 | Dolensky et al. |
| 8,192,526 | B2 | 6/2012 | Zhong et al. |
| 8,210,205 | B2 | 7/2012 | Michaels |
| 8,225,789 | B2 | 7/2012 | Berthon-jones |
| 8,226,745 | B2 | 7/2012 | Siew-wah et al. |
| 8,236,095 | B1 | 8/2012 | Bassine |
| 8,256,419 | B2 | 9/2012 | Sinderby et al. |
| 8,257,473 | B2 | 9/2012 | Mccombs et al. |
| 8,280,498 | B2 | 10/2012 | Jalde |
| 8,282,717 | B2 | 10/2012 | Chambers et al. |
| 8,297,279 | B2 | 10/2012 | Devries et al. |
| 8,337,599 | B2 | 12/2012 | Kiritake |
| 8,343,259 | B2 | 1/2013 | Knaebel |
| 8,349,053 | B2 | 1/2013 | Lee et al. |
| 8,361,204 | B1 | 1/2013 | Bassine |
| 8,366,815 | B2 | 2/2013 | Taylor et al. |
| 8,371,298 | B2 | 2/2013 | Hallback et al. |
| 8,375,944 | B2 | 2/2013 | Kwok |
| 8,377,180 | B2 | 2/2013 | Maeda et al. |
| 8,377,181 | B2 | 2/2013 | Taylor et al. |
| 8,388,548 | B2 | 3/2013 | Green et al. |
| 8,388,745 | B1 | 3/2013 | Pelletier et al. |
| 8,400,290 | B2 | 3/2013 | Baker, Jr. |
| 8,418,691 | B2 | 4/2013 | Jafari et al. |
| 8,418,692 | B2 | 4/2013 | Sanchez |
| 8,424,520 | B2 | 4/2013 | Thiessen |
| 8,424,521 | B2 | 4/2013 | Jafari et al. |
| 8,428,672 | B2 | 4/2013 | Sherman et al. |
| 8,434,480 | B2 | 5/2013 | Jafari et al. |
| 8,434,482 | B2 | 5/2013 | Borrello |
| 8,434,488 | B2 | 5/2013 | Li et al. |
| 8,435,013 | B2 | 5/2013 | Kondou et al. |
| 8,440,004 | B2 | 5/2013 | Taylor et al. |
| 8,443,294 | B2 | 5/2013 | Skidmore et al. |
| 8,448,640 | B2 | 5/2013 | Bassin |
| 8,448,641 | B2 | 5/2013 | Jafari et al. |
| 8,469,026 | B2 | 6/2013 | Blomberg et al. |
| 8,522,780 | B2 | 9/2013 | Devries et al. |
| 8,539,952 | B2 | 9/2013 | Carbone et al. |
| 8,627,819 | B2 | 1/2014 | Devries et al. |
| 8,683,997 | B2 | 4/2014 | Devries et al. |
| 8,770,191 | B2 | 7/2014 | Tham |
| 8,844,530 | B2 | 9/2014 | Bimkrant |
| 9,126,002 | B2 | 9/2015 | Devries et al. |
| 9,345,851 | B2 | 5/2016 | Kim et al. |
| 9,504,799 | B2 | 11/2016 | Hardin et al. |
| 9,522,248 | B2 | 12/2016 | Martin |
| 9,956,371 | B2 | 5/2018 | DeVries |
| 10,046,134 | B2 | 8/2018 | DeVries |
| 10,105,509 | B2 | 10/2018 | DeVries |
| 10,245,406 | B2 | 4/2019 | Devries |
| 10,315,002 | B2 | 6/2019 | Devries et al. |
| 10,350,377 | B2 | 7/2019 | Fiorenza |
| 10,518,059 | B2 | 12/2019 | Cipollone et al. |
| 10,758,699 | B2 | 9/2020 | Cipollone et al. |
| 10,773,049 | B2 | 9/2020 | Gaw et al. |
| 11,191,915 | B2 | 12/2021 | Ahmad |
| 2002/0005197 | A1 | 1/2002 | DeVries |
| 2002/0053286 | A1 | 5/2002 | Czabala |
| 2002/0092420 | A1 | 7/2002 | Jagger et al. |
| 2002/0121278 | A1 | 9/2002 | Hete |
| 2003/0000531 | A1 | 1/2003 | Tuck |
| 2003/0010208 | A1 | 1/2003 | Jagger et al. |
| 2003/0024766 | A1 | 2/2003 | Briscoe |
| 2003/0051729 | A1 | 3/2003 | Be et al. |
| 2003/0111077 | A1 | 6/2003 | Van Hooser |
| 2003/0131848 | A1 | 7/2003 | Stenzler |
| 2003/0196550 | A1 | 10/2003 | Keefer et al. |
| 2003/0200865 | A1 | 10/2003 | Mccombs et al. |
| 2003/0230308 | A1 | 12/2003 | Linden |
| 2004/0021108 | A1 | 2/2004 | Hallback et al. |
| 2004/0060560 | A1 | 4/2004 | Stenzler et al. |
| 2004/0231913 | A1 | 11/2004 | Mccombs et al. |
| 2005/0012657 | A1 | 1/2005 | Mohan |
| 2005/0045040 | A1 | 3/2005 | Mccombs |
| 2005/0072298 | A1 | 4/2005 | Deane et al. |
| 2005/0072306 | A1 | 4/2005 | Deane et al. |
| 2005/0072423 | A1 | 4/2005 | Deane et al. |
| 2005/0072426 | A1 | 4/2005 | Deane et al. |
| 2005/0103341 | A1 | 5/2005 | Deane et al. |
| 2005/0112013 | A1 | 5/2005 | Devries et al. |
| 2005/0217481 | A1 | 10/2005 | Dunne et al. |
| 2005/0257686 | A1 | 11/2005 | Occhialini et al. |
| 2005/0274381 | A1 | 12/2005 | Deane et al. |
| 2005/0274815 | A1 | 12/2005 | Bergholtz et al. |
| 2006/0011065 | A1 | 1/2006 | Hastings |
| 2006/0042631 | A1 | 3/2006 | Martin et al. |
| 2006/0064802 | A1 | 3/2006 | Damrath et al. |
| 2006/0086251 | A1 | 4/2006 | Sprinkle |
| 2006/0102181 | A1 | 5/2006 | Mccombs et al. |
| 2006/0107947 | A1 | 5/2006 | Rist |
| 2006/0117957 | A1 | 6/2006 | Mccombs et al. |
| 2006/0137522 | A1 | 6/2006 | Nishimura et al. |
| 2006/0144240 | A1 | 7/2006 | Lee et al. |
| 2006/0174871 | A1 | 8/2006 | Jagger et al. |
| 2006/0174875 | A1 | 8/2006 | Jagger et al. |
| 2006/0174877 | A1 | 8/2006 | Jagger et al. |
| 2006/0230924 | A1 | 10/2006 | Deane et al. |
| 2006/0230929 | A1 | 10/2006 | Bliss et al. |
| 2006/0230931 | A1 | 10/2006 | Bliss et al. |
| 2006/0230939 | A1 | 10/2006 | Bliss et al. |
| 2006/0266357 | A1 | 11/2006 | Mccombs et al. |
| 2006/0283325 | A1 | 12/2006 | Sugano |
| 2006/0283447 | A1 | 12/2006 | Dhuper et al. |
| 2007/0031302 | A1 | 2/2007 | Wittrup et al. |
| 2007/0056583 | A1 | 3/2007 | Jagger et al. |
| 2007/0056584 | A1 | 3/2007 | Jagger et al. |
| 2007/0084342 | A1 | 4/2007 | Hunter et al. |
| 2007/0084349 | A1 | 4/2007 | Calkins et al. |
| 2007/0101999 | A1 | 5/2007 | Duquette et al. |
| 2007/0135757 | A1 | 6/2007 | Acker |
| 2007/0144521 | A1 | 6/2007 | Devries et al. |
| 2007/0148016 | A1 | 6/2007 | Crawford et al. |
| 2007/0169623 | A1 | 7/2007 | Lee et al. |
| 2007/0199566 | A1 | 8/2007 | Be |
| 2007/0214955 | A1 | 9/2007 | Aylsworth et al. |
| 2007/0227360 | A1 | 10/2007 | Atlas et al. |
| 2007/0227540 | A1 | 10/2007 | Ljungberg et al. |
| 2007/0272243 | A1 | 11/2007 | Sherman et al. |
| 2007/0289446 | A1 | 12/2007 | Occhialini et al. |
| 2008/0000477 | A1 | 1/2008 | Huster et al. |
| 2008/0004566 | A1 | 1/2008 | Sloan |
| 2008/0028933 | A1 | 2/2008 | Ross et al. |
| 2008/0034975 | A1 | 2/2008 | Chambers et al. |
| 2008/0053441 | A1 | 3/2008 | Gottlib |
| 2008/0066616 | A1 | 3/2008 | Sprinkle |

(56) References Cited

U.S. PATENT DOCUMENTS

| | | | |
|---|---|---|---|
| 2008/0066741 | A1 | 3/2008 | LeMahieu et al. |
| 2008/0087170 | A1 | 4/2008 | Deane et al. |
| 2008/0092892 | A1 | 4/2008 | Boyle et al. |
| 2008/0092893 | A1 | 4/2008 | Boyle et al. |
| 2008/0110338 | A1 | 5/2008 | Taylor et al. |
| 2008/0110451 | A1 | 5/2008 | Dunsmore et al. |
| 2008/0110461 | A1 | 5/2008 | Mulqueeny et al. |
| 2008/0135044 | A1 | 6/2008 | Freitag et al. |
| 2008/0185544 | A1 | 8/2008 | Yeh |
| 2008/0196580 | A1 | 8/2008 | Bliss et al. |
| 2008/0202337 | A1 | 8/2008 | Taylor et al. |
| 2008/0202508 | A1 | 8/2008 | Mcclain et al. |
| 2008/0251071 | A1 | 10/2008 | Armitstead et al. |
| 2008/0257145 | A1 | 10/2008 | Sprinkle et al. |
| 2008/0257349 | A1 | 10/2008 | Hedner et al. |
| 2008/0282880 | A1 | 11/2008 | Bliss et al. |
| 2008/0295839 | A1 | 12/2008 | Habashi |
| 2008/0302362 | A1 | 12/2008 | Kwok |
| 2008/0302363 | A1 | 12/2008 | Kroupa |
| 2008/0314385 | A1 | 12/2008 | Brunner et al. |
| 2008/0315441 | A1 | 12/2008 | Lee et al. |
| 2009/0007912 | A1 | 1/2009 | Lindell et al. |
| 2009/0025560 | A1 | 1/2009 | Takemasa |
| 2009/0025564 | A1 | 1/2009 | Kuwabara |
| 2009/0044698 | A1 | 2/2009 | Meacham |
| 2009/0065007 | A1 | 3/2009 | Wilkinson et al. |
| 2009/0065526 | A1 | 3/2009 | Sprinkle |
| 2009/0071333 | A1 | 3/2009 | Labuda et al. |
| 2009/0078251 | A1 | 3/2009 | Zucchi et al. |
| 2009/0084381 | A1 | 4/2009 | Devries et al. |
| 2009/0101147 | A1 | 4/2009 | Landis et al. |
| 2009/0107500 | A1 | 4/2009 | Edwards |
| 2009/0133368 | A1 | 5/2009 | Calkins et al. |
| 2009/0133694 | A1 | 5/2009 | Solci et al. |
| 2009/0145428 | A1 | 6/2009 | Sward et al. |
| 2009/0167698 | A1 | 7/2009 | Altas et al. |
| 2009/0188502 | A1 | 7/2009 | Tiedje |
| 2009/0211448 | A1 | 8/2009 | Mcclain |
| 2009/0229459 | A1 | 9/2009 | Warren et al. |
| 2009/0250059 | A1 | 10/2009 | Allum et al. |
| 2009/0301477 | A1 | 12/2009 | Pierro et al. |
| 2009/0308396 | A1 | 12/2009 | Mcclain |
| 2010/0024819 | A1 | 2/2010 | Tiedje |
| 2010/0051030 | A1 | 3/2010 | Richard et al. |
| 2010/0052293 | A1 | 3/2010 | Brooks et al. |
| 2010/0071693 | A1 | 3/2010 | Allum et al. |
| 2010/0078018 | A1 | 4/2010 | Heinonen |
| 2010/0095841 | A1 | 4/2010 | Naheiri |
| 2010/0116270 | A1 | 5/2010 | Branson et al. |
| 2010/0122699 | A1 | 5/2010 | Birnkrant |
| 2010/0126249 | A1 | 5/2010 | Matsuzaki |
| 2010/0154797 | A1 | 6/2010 | Landis et al. |
| 2010/0229867 | A1 | 9/2010 | Bertinetti et al. |
| 2010/0275921 | A1 | 11/2010 | Schindhelm et al. |
| 2010/0282084 | A1 | 11/2010 | Hansen et al. |
| 2010/0288279 | A1 | 11/2010 | Seiver et al. |
| 2010/0294127 | A1 | 11/2010 | Dolensky |
| 2011/0000489 | A1 | 1/2011 | Laksov et al. |
| 2011/0030684 | A1 | 2/2011 | Wilkinson et al. |
| 2011/0030685 | A1 | 2/2011 | Wilkinson et al. |
| 2011/0030686 | A1 | 2/2011 | Wilkinson et al. |
| 2011/0030687 | A1 | 2/2011 | Wilkinson et al. |
| 2011/0030689 | A1 | 2/2011 | Wilkinson et al. |
| 2011/0057651 | A1 | 3/2011 | Duric et al. |
| 2011/0067699 | A1 | 3/2011 | Caruso et al. |
| 2011/0073107 | A1 | 3/2011 | Rodman et al. |
| 2011/0073115 | A1 | 3/2011 | Wood et al. |
| 2011/0113964 | A1 | 5/2011 | Chambers et al. |
| 2011/0154986 | A1 | 6/2011 | Lee et al. |
| 2011/0192122 | A1 | 8/2011 | Whitesel et al. |
| 2011/0197882 | A1 | 8/2011 | Truschel et al. |
| 2011/0197883 | A1 | 8/2011 | Mcdaniel et al. |
| 2011/0197884 | A1 | 8/2011 | Duff et al. |
| 2011/0197887 | A1 | 8/2011 | Truschel et al. |
| 2011/0197889 | A1 | 8/2011 | Lahde et al. |
| 2011/0209706 | A1 | 9/2011 | Truschel et al. |
| 2011/0209707 | A1 | 9/2011 | Terhark |
| 2011/0220107 | A1 | 9/2011 | Kimm et al. |
| 2011/0232483 | A1 | 9/2011 | Haberland et al. |
| 2011/0232645 | A1 | 9/2011 | Smith |
| 2011/0247616 | A1 | 10/2011 | Von Hollen et al. |
| 2011/0247620 | A1 | 10/2011 | Armstrong et al. |
| 2011/0247621 | A1 | 10/2011 | Richard et al. |
| 2011/0247622 | A1 | 10/2011 | Schneider et al. |
| 2011/0259334 | A1 | 10/2011 | Alfieri et al. |
| 2011/0297153 | A1 | 12/2011 | Grimsey |
| 2011/0303223 | A1 | 12/2011 | Kane et al. |
| 2011/0315140 | A1 | 12/2011 | Shuman |
| 2012/0000462 | A1 | 1/2012 | Edwards et al. |
| 2012/0006199 | A1 | 1/2012 | Mccombs et al. |
| 2012/0006326 | A1 | 1/2012 | Ahmad |
| 2012/0012109 | A1 | 1/2012 | Chalvignac |
| 2012/0017909 | A1 | 1/2012 | Porges et al. |
| 2012/0027628 | A1 | 2/2012 | Ogawa |
| 2012/0037159 | A1 | 2/2012 | Mulqueeny et al. |
| 2012/0055340 | A1 | 3/2012 | Wilkinson et al. |
| 2012/0055474 | A1 | 3/2012 | Wilkinson |
| 2012/0055475 | A1 | 3/2012 | Wilkinson |
| 2012/0055477 | A1 | 3/2012 | Wilkinson |
| 2012/0055480 | A1 | 3/2012 | Wilkinson |
| 2012/0055482 | A1 | 3/2012 | Wilkinson |
| 2012/0055483 | A1 | 3/2012 | Wilkinson et al. |
| 2012/0060840 | A1 | 3/2012 | Refsland et al. |
| 2012/0125336 | A1 | 5/2012 | Berthon-jones et al. |
| 2012/0125337 | A1 | 5/2012 | Asanoi |
| 2012/0152248 | A1 | 6/2012 | Richey, II et al. |
| 2012/0167883 | A1 | 7/2012 | Taylor et al. |
| 2012/0167886 | A1 | 7/2012 | Taylor et al. |
| 2012/0167887 | A1 | 7/2012 | Taylor et al. |
| 2012/0167888 | A1 | 7/2012 | Taylor et al. |
| 2012/0174926 | A1 | 7/2012 | Tham |
| 2012/0177546 | A1 | 7/2012 | Hilbig |
| 2012/0192862 | A1 | 8/2012 | Lewis et al. |
| 2012/0192864 | A1 | 8/2012 | Galbraith et al. |
| 2012/0192867 | A1 | 8/2012 | Lewis et al. |
| 2012/0247329 | A1 | 10/2012 | Hilbig |
| 2012/0266883 | A1 | 10/2012 | Taylor et al. |
| 2012/0285460 | A1 | 11/2012 | Smith et al. |
| 2012/0285543 | A1 | 11/2012 | Michaels |
| 2012/0291884 | A1 | 11/2012 | Yamaura et al. |
| 2012/0304867 | A1 | 12/2012 | Watanabe et al. |
| 2012/0308779 | A1 | 12/2012 | Klee et al. |
| 2012/0318145 | A1 | 12/2012 | Hilbig et al. |
| 2013/0008438 | A1 | 1/2013 | Sugawara et al. |
| 2013/0008444 | A1 | 1/2013 | Chalvignac et al. |
| 2013/0025591 | A1 | 1/2013 | Clark et al. |
| 2013/0031784 | A1 | 2/2013 | Chambers et al. |
| 2013/0032148 | A1 | 2/2013 | Neely |
| 2013/0081617 | A1 | 4/2013 | Cavendish |
| 2013/0087145 | A1 | 4/2013 | Koebrich et al. |
| 2013/0087146 | A1 | 4/2013 | Callaghan et al. |
| 2013/0092159 | A1 | 4/2013 | Ulrichskoetter et al. |
| 2013/0098361 | A1 | 4/2013 | Koebrich et al. |
| 2013/0104898 | A1 | 5/2013 | Berthon-jones |
| 2013/0125891 | A1 | 5/2013 | Eddy |
| 2013/0167843 | A1 | 7/2013 | Kimm et al. |
| 2013/0186400 | A1 | 7/2013 | Jafari et al. |
| 2013/0186401 | A1 | 7/2013 | Jafari et al. |
| 2013/0199520 | A1 | 8/2013 | Dhuper et al. |
| 2013/0220325 | A1 | 8/2013 | Davis et al. |
| 2013/0255689 | A1 | 10/2013 | Kim et al. |
| 2013/0272905 | A1 | 10/2013 | Shelke |
| 2013/0276789 | A1 | 10/2013 | Garde et al. |
| 2013/0312757 | A1 | 11/2013 | Gragg et al. |
| 2014/0007878 | A1 | 1/2014 | Armistead et al. |
| 2014/0116441 | A1 | 5/2014 | Mcdaniel |
| 2014/0150789 | A1 | 6/2014 | Flanagan et al. |
| 2014/0150791 | A1 | 6/2014 | Bimkrant et al. |
| 2014/0150792 | A1 | 6/2014 | Christopher et al. |
| 2014/0166009 | A1 | 6/2014 | Flanagan et al. |
| 2014/0216446 | A1 | 8/2014 | Wruck |
| 2014/0283834 | A1 | 9/2014 | Ahmad et al. |
| 2014/0318535 | A1 | 10/2014 | Bullock |
| 2014/0373835 | A1 | 12/2014 | Ahmad et al. |

(56) References Cited

U.S. PATENT DOCUMENTS

| | | | |
|---|---|---|---|
| 2015/0000654 | A1 | 1/2015 | Martin |
| 2015/0000660 | A1 | 1/2015 | Martin |
| 2015/0027444 | A1 | 1/2015 | Col, Jr. |
| 2015/0101610 | A1 | 4/2015 | Nitta |
| 2015/0224278 | A1 | 8/2015 | Addington et al. |
| 2015/0283352 | A1 | 10/2015 | Karkkainen |
| 2015/0320962 | A1 | 11/2015 | Bafile |
| 2016/0095997 | A1 | 4/2016 | Kapust et al. |
| 2016/0129213 | A1 | 5/2016 | Zhu et al. |
| 2016/0243330 | A1 | 8/2016 | Destefano |
| 2016/0279369 | A1 | 9/2016 | Cipollone |
| 2016/0279378 | A1 | 9/2016 | Cipollone et al. |
| 2017/0000968 | A1 | 1/2017 | Harrington et al. |
| 2017/0361058 | A1 | 12/2017 | Gaw et al. |
| 2018/0085541 | A1 | 3/2018 | Ye et al. |
| 2019/0054268 | A1 | 2/2019 | DeVries |
| 2019/0099570 | A1 | 4/2019 | Brambilla et al. |
| 2019/0175856 | A1* | 6/2019 | Galbraith .......... A61M 16/0066 |
| 2019/0344033 | A1 | 11/2019 | Ahmad |
| 2021/0252243 | A1 | 8/2021 | Barlow et al. |

FOREIGN PATENT DOCUMENTS

| | | | |
|---|---|---|---|
| CN | 201065977 | Y | 5/2008 |
| CN | 201240850 | Y | 5/2009 |
| CN | 201273451 | Y | 7/2009 |
| CN | 101765443 | A | 6/2010 |
| CN | 101962125 | A | 2/2011 |
| CN | 102300599 | A | 12/2011 |
| CN | 102500030 | A | 6/2012 |
| CN | 103071215 | A | 5/2013 |
| CN | 103384541 | A | 11/2013 |
| CN | 203943984 | U | 11/2014 |
| CN | 203988387 | U | 12/2014 |
| CN | 204307184 | U | 5/2015 |
| CN | 204917961 | U | 12/2015 |
| CN | 112587771 | A | 4/2021 |
| CN | 112587772 | A | 4/2021 |
| EP | 0937478 | B1 | 8/2003 |
| GB | 2164568 | A | 3/1986 |
| GB | 2485417 | A | 5/2012 |
| JP | 59116041 | A | 7/1984 |
| JP | H11-192410 | A | 7/1999 |
| JP | H11-210927 | A | 8/1999 |
| JP | 2000024110 | A | 1/2000 |
| JP | 2000102617 | A | 4/2000 |
| JP | 2000300672 | A | 10/2000 |
| JP | 2000300673 | A | 10/2000 |
| JP | 2001120660 | A | 5/2001 |
| JP | 2001507982 | A | 6/2001 |
| JP | 2002136598 | A | 5/2002 |
| JP | 2003156174 | A | 5/2003 |
| JP | 2007117273 | A | 5/2007 |
| JP | 2008501445 | A | 1/2008 |
| JP | 2008539841 | A | 11/2008 |
| JP | 2010535078 | A | 11/2010 |
| JP | 2012508074 | A | 4/2012 |
| JP | 201418030 | A | 9/2014 |
| JP | 2015080699 | A | 4/2015 |
| KR | 20130123640 | A | 11/2013 |
| WO | 1998022172 | A | 5/1998 |
| WO | 1998026830 | A | 6/1998 |
| WO | 1999008738 | A1 | 2/1999 |
| WO | 2000038772 | A1 | 7/2000 |
| WO | 2003008017 | A2 | 1/2003 |
| WO | 2003045486 | A1 | 6/2003 |
| WO | 2004004815 | A1 | 1/2004 |
| WO | 2005025658 | A1 | 3/2005 |
| WO | 2006102345 | A1 | 9/2006 |
| WO | 2006121980 | A2 | 11/2006 |
| WO | 2009105597 | A1 | 8/2009 |
| WO | 2010054323 | A3 | 5/2010 |
| WO | 2010058308 | A2 | 5/2010 |
| WO | 2010141983 | A1 | 12/2010 |
| WO | 2011161060 | A1 | 12/2011 |
| WO | 2012052903 | A1 | 4/2012 |
| WO | 2013033589 | A1 | 3/2013 |
| WO | 2013067592 | A1 | 5/2013 |
| WO | 2013140321 | A1 | 9/2013 |
| WO | 2013164733 | A1 | 11/2013 |
| WO | 2014059405 | A1 | 4/2014 |
| WO | 2014089188 | A1 | 6/2014 |
| WO | 2014135997 | A1 | 9/2014 |
| WO | 2014176454 | A1 | 10/2014 |
| WO | 2015015394 | A1 | 2/2015 |
| WO | 2015126853 | A1 | 8/2015 |
| WO | 2015192186 | A1 | 12/2015 |
| WO | 2016067147 | A1 | 5/2016 |
| WO | 2017149532 | A1 | 9/2017 |
| WO | 2019191814 | A1 | 10/2019 |

OTHER PUBLICATIONS

Branson, D R. et al., Branson, D. Richard et al., "Maximizing Oxygen Delivery During Mechanical Ventilation with a Portable Oxygen Concentrator," The Journal of TRAUMA® Injury, Infection, and Critical Care, vol. 69, No. 1, Supplement Jul. 2010, 7 pages., Jul. 2010, 7 pages.

International Search Report and Written Opinion mailed Aug. 8, 2019 in International Patent Application No. PCT/US2019/027094, 13 pages.

International Search Report and Written Opinion mailed Mar. 17, 2022 in International Patent Application No. PCT/US2021/064722, 12 pages.

International Search Report and Written Opinion mailed Aug. 2, 2022 in International Patent Application No. PCT/US2022/071677, 19 pages.

Chinese Office Action (Notice of Allowance) with English translation mailed Apr. 28, 2024 in Chinese Patent Application No. 202011330634.5, 7 pages.

Chinese Office Action with English translation mailed Apr. 20, 2024 in Chinese Patent Application No. 202011442606.2, 9 pages.

Chinese Office Action with English translation malled Jul. 27, 2024 in Chinese Patent Application No. 202011387869.8, 16 pages.

Chinese Office Action with English translation mailed Mar. 16, 2024 in Chinese Patent Application No. 202011387876.8, 23 pages.

Extended European Search Report mailed on Oct. 8, 2024 in European Patent Application No. 21912087.0, 11 pages.

Japanese Office Action with English translation mailed Nov. 13, 2023 in Japanese Patent Application No. 2021-514284, 8 pages.

Japanese Office Action with translation mailed Oct. 3, 2024 in Japanese Patent Application No. 2023-76384, 6 pages.

Extedned European Search Report mailed on Oct. 8, 2024 in European Patent Application No. 21912087.0, 11 pages.

* cited by examiner

VENTILATOR SYSTEMS WITH INTEGRATED OXYGEN DELIVERY, AND ASSOCIATED DEVICES AND METHODS

CROSS-REFERENCE TO RELATED APPLICATION(S)

The present application claims priority to U.S. Provisional Application No. 63/128,739, filed Dec. 21, 2020, and titled "VENTILATOR SYSTEMS WITH INTEGRATED OXYGEN DELIVERY, AND ASSOCIATED DEVICES AND METHODS," the disclosure of which is incorporated by reference herein in its entirety.

TECHNICAL FIELD

The present technology is generally directed to ventilator systems, and in particular to ventilator systems that can deliver oxygen therapy, ventilation therapy, and/or both oxygen and ventilation therapy.

BACKGROUND

Mechanical ventilators are used to assist with breathing. For example, conventional mechanical ventilators typically drive inspiratory gases into the patient's lungs to assist with the patient's breathing. However, many patients who use a ventilator do not require constant mechanical ventilation. Instead, at various times throughout the day, they may prefer to only receive supplemental oxygen, such as pulses of oxygen received from a conventional portable oxygen concentrator. Patients who at times require mechanical ventilation and at times prefer supplemental oxygen generally have multiple different machines, including a ventilator and an oxygen concentrator, for providing these different therapies. Unfortunately, having to rely on multiple machines reduces the independence of the patient (e.g., they may not wish to leave the house without both machines) and increases the logistical burden of switching between therapy options. Accordingly, a need exists for improved systems that provide a patient with a variety of therapy options to suit their evolving needs.

BRIEF DESCRIPTION OF THE DRAWINGS

Many aspects of the present technology can be better understood with reference to the following drawings. The components in the drawings are not necessarily to scale. Instead, emphasis is placed on clearly illustrating the principles of the present technology.

DETAILED DESCRIPTION

Figure 1A:
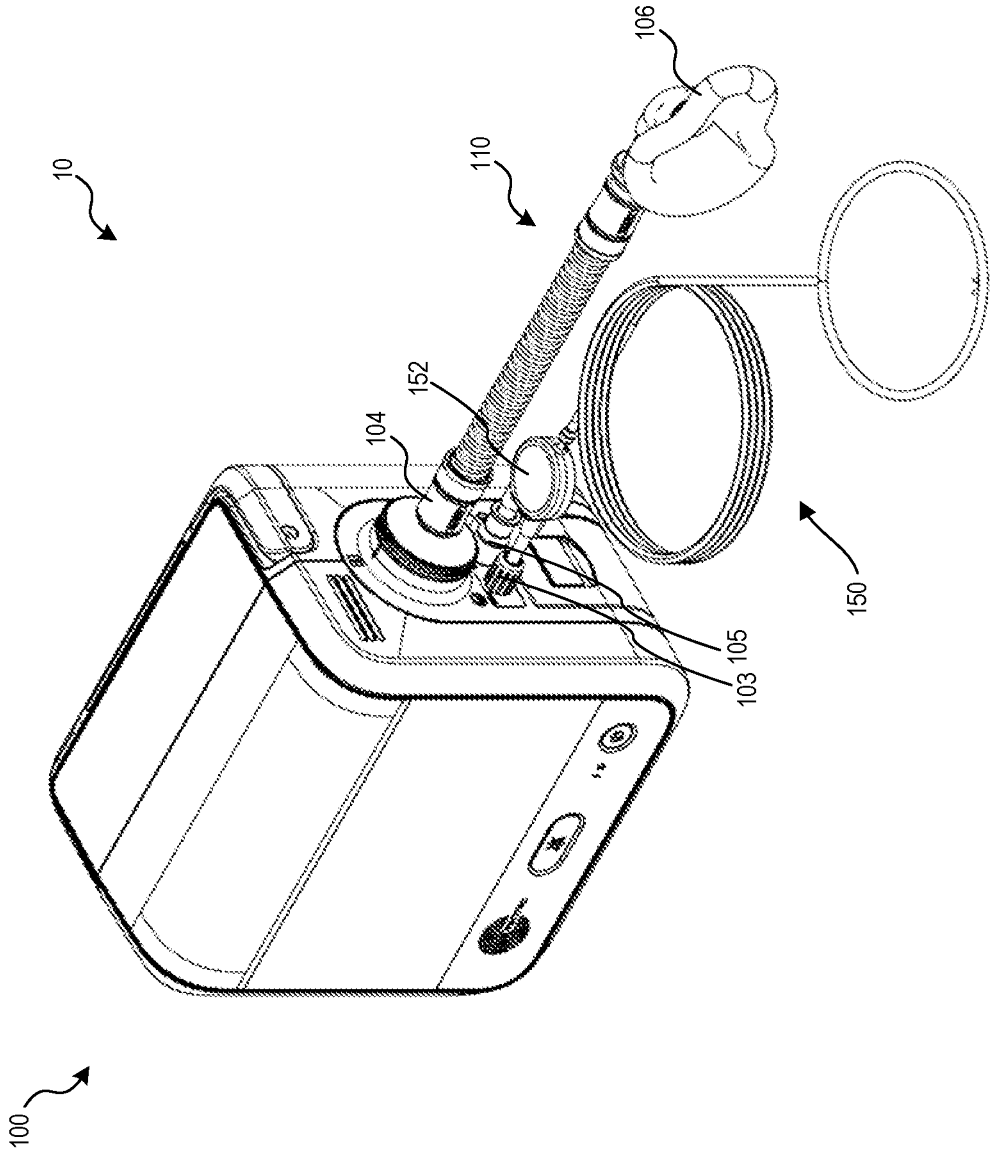
FIG. 1A is an isometric view of a ventilator system including an oxygen delivery circuit and a patient circuit and configured in accordance with embodiments of the present technology.

The present technology is directed to ventilator systems that can provide both ventilation therapy and oxygen therapy. For example, in some embodiments the systems described herein include a ventilation assembly that can provide inspiratory gas to a patient circuit to support the patient's breathing. The patient circuit can route the inspiratory gas to the patient. The systems described herein can also include an oxygen assembly that can provide pulses of oxygen to an oxygen delivery circuit. The oxygen delivery circuit can route the pulses of oxygen to the patient. In some embodiments, the oxygen delivery circuit is distinct from the patient circuit. For example, the patient circuit can include a corrugated conduit coupled to a ventilation mask, and the oxygen delivery circuit can include a nasal cannula. The ventilation mask can be positioned over the nasal cannula so that the patient can receive both the inspiratory gases and the pulses of oxygen.

In some embodiments, the systems described herein can deliver oxygen to a patient independent of delivering ventilation therapy to a patient. For example, a patient can use the ventilator systems to solely receive pulses of supplemental oxygen through a nasal cannula, similar to patients using conventional portable oxygen concentrators. Likewise, the systems described herein can be used to deliver ventilation therapy to a patient independent of or in combination with the pulses of the oxygen. For example, a patient can receive the ventilation gases mixed with oxygen via a patient connection such as a ventilator mask or tracheal tube. As another example, a patient can receive the ventilation gases through a first patient connection (e.g., a ventilator mask), and simultaneously receive the pulses of oxygen through a second patient connection (e.g., a nasal cannula).

The systems described herein therefore provide flexible therapy options to meet evolving patient needs. For example, in some embodiments the systems described herein can (1) deliver pulses of supplemental oxygen to a patient independent of delivering ventilation therapy to the patient, (2) deliver ventilation therapy to a patient independent of delivering supplemental oxygen to the patient, and (3) simultaneously deliver ventilation gases and pulses of oxygen to the patient, either through the same or different patient connection. Providing a variety of therapy options from a single portable ventilator is expected to improve patients' quality of life by decreasing the number of breathing support devices and systems the patient must rely upon and/or by more precisely tailoring the type and level of therapy a patient needs, which may fluctuate throughout the day and/or over time.

Further aspects and advantages of the devices, methods, and uses will become apparent from the ensuing description that is given by way of example only.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-9.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. The term "substantially" or grammatical variations thereof refers to at least about 50%, for example, 75%, 85%, 95%, or 98%.

FIG. 1A is an isometric view of a system 10 including a ventilator 100, a patient circuit 110, and an oxygen delivery circuit 150 (shown as a cannula) and configured in accordance with embodiments of the present technology. The ventilator 100 may be configured to be portable and powered by an internal battery (not shown) and/or an external power source (not shown) such as a conventional wall outlet. The ventilator 100 can have a main ventilator connection 104 (which may also be referred to herein as an "inspiratory gas outlet port" or a "ventilation port") for delivering breathing gases to the patient circuit 110 for delivery to a patient. As described in greater detail below, the patient circuit 110 can include a patient connection 106 (shown as a mask) for coupling to the patient. The ventilator 100 can further include an oxygen outlet port 105 for delivering a bolus or pulse of oxygen from the ventilator 100 to the oxygen delivery circuit 150 for delivery to the patient. As illustrated, the oxygen delivery circuit 150 is distinct from the patient circuit 110. For example, the patient circuit 110 and the oxygen delivery circuit 150 are coupled to the ventilator at different ports (e.g., the main ventilator connection 104 versus the oxygen outlet port 105) and are also coupleable to the patient via different patient connection interfaces (e.g., the patient circuit 110 is coupleable to the patient via a mask and the oxygen delivery circuit 150 is coupleable to the patient via a nasal cannula).

The ventilator 100 can further include a breath sensing port 103. The breath sensing port 103 can include one or more transducers or sensors (e.g., sensors 208, shown in FIG. 2) for measuring one or more parameters of a patient's breath and/or within the system (e.g., flow, pressure, volume, etc.). In some embodiments, the breath sensing port 103 can be a multi-lumen tube connection such as described in U.S. Pat. Nos. 10,245,406 and 10,315,002, the disclosures of which are incorporated by reference herein in their entireties and for all purposes. The measured parameter can be used to trigger delivery of the breathing gases through the main ventilator connection 104 and/or the pulses of oxygen through the oxygen outlet port 105.

The system 10 can further include an adapter 152 positionable between the oxygen delivery circuit 150 and the ventilator 100. The adapter 152 can interface with (e.g., plug into) both the oxygen outlet port 105 and the breath sensing port 103. As described in detail below with respect to FIGS. 2-7B, the adapter 152 enables oxygen to flow from the ventilator 100 to the oxygen delivery circuit 150 while simultaneously permitting patient inspiratory efforts to be detected by the breath sensing port 103, thereby enabling delivery of oxygen pulses synchronized with the patient's breath. The adapter 152 can also be configured to protect the sensors of the breath sensing port 103 from being damaged from the relatively high-pressure delivery of oxygen pulses.

Figure 1B:
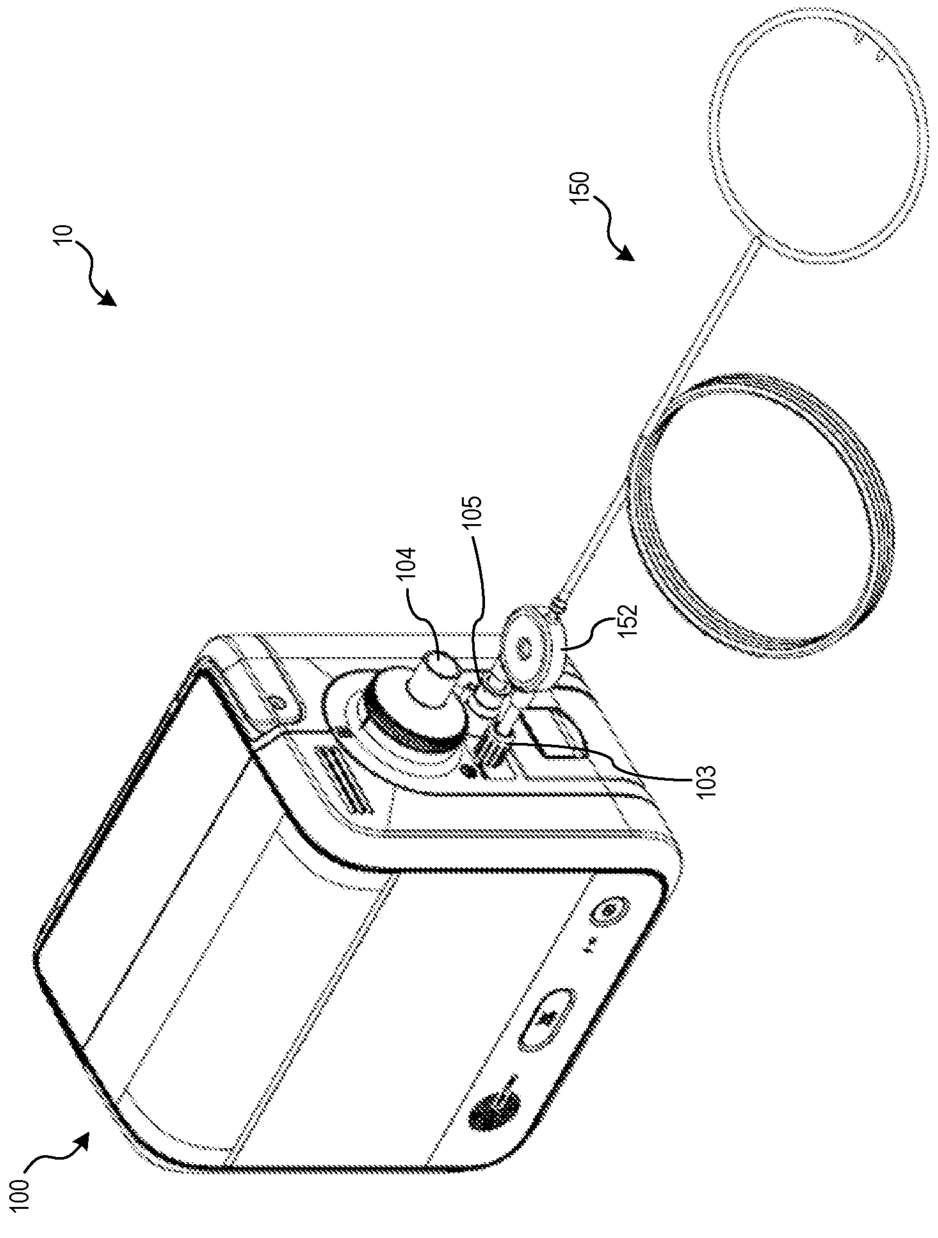
FIG. 1B is an isometric view of the ventilator system shown in FIG. 1A with the patient circuit omitted.
Figure 1C:
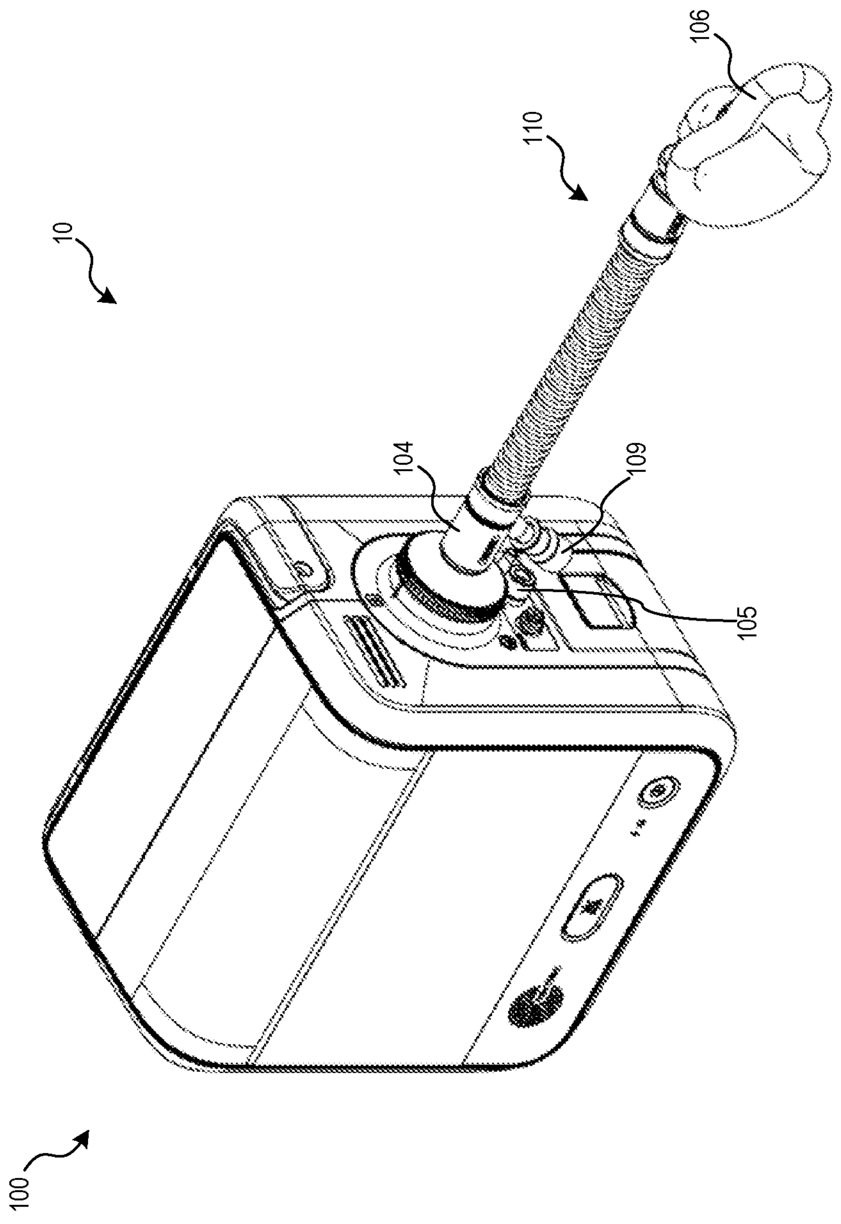
FIG. 1C is an isometric view of the ventilator system shown in FIG. 1A with the oxygen delivery circuit omitted.

As described in greater detail below, the ventilator 100 can deliver oxygen to a patient independent of the ventilation therapy and/or in combination with the ventilation therapy. For example, the system 10 can operate in an oxygen mode in which it provides pulses of oxygen to the patient, a ventilation mode in which it provides inspiratory gases to the patient, and/or a combination mode in which it provides both inspiratory gases and pulses of oxygen to the patient. The ventilator 100 can operate in any of the foregoing modes when both the patient circuit 110 and the oxygen delivery circuit 150 are coupled to the ventilator 100 as shown in FIG. 1A (e.g., even though the patient circuit 110 is coupled to the ventilator 100, the ventilator 100 can still be used to solely provide supplemental oxygen via the oxygen delivery circuit 150). However, other configurations are possible. For example, FIG. 1B illustrates a configuration in which the oxygen delivery circuit 150 is coupled to the ventilator 100, but the patient circuit 110 is not (e.g., for use in the oxygen mode). FIG. 1C illustrates an additional configuration in which a patient circuit 110 is coupled to the ventilator 100, but the oxygen delivery circuit 150 is not (e.g., for use in the ventilation mode). As also shown in FIG. 1C, the patient circuit 110 may optionally have an oxygen lumen 109 that can be coupled to the oxygen outlet port 105 such that both inspiratory gases and oxygen can be delivered to the patient via the patient circuit 110 (e.g., for use in the combination mode). In such embodiments, the oxygen delivery circuit 150 is not required for the combination mode, although it can still be used if desired. The system 10 can be easily transitioned between the three configurations shown in FIGS. 1A-1C by simply coupling or decoupling the patient circuit 110 and/or the oxygen delivery circuit 150 to or from the ventilator 100. Accordingly, the selected configuration may be based on user preference, mode of operation, availability of components, or the like.

Figure 2:
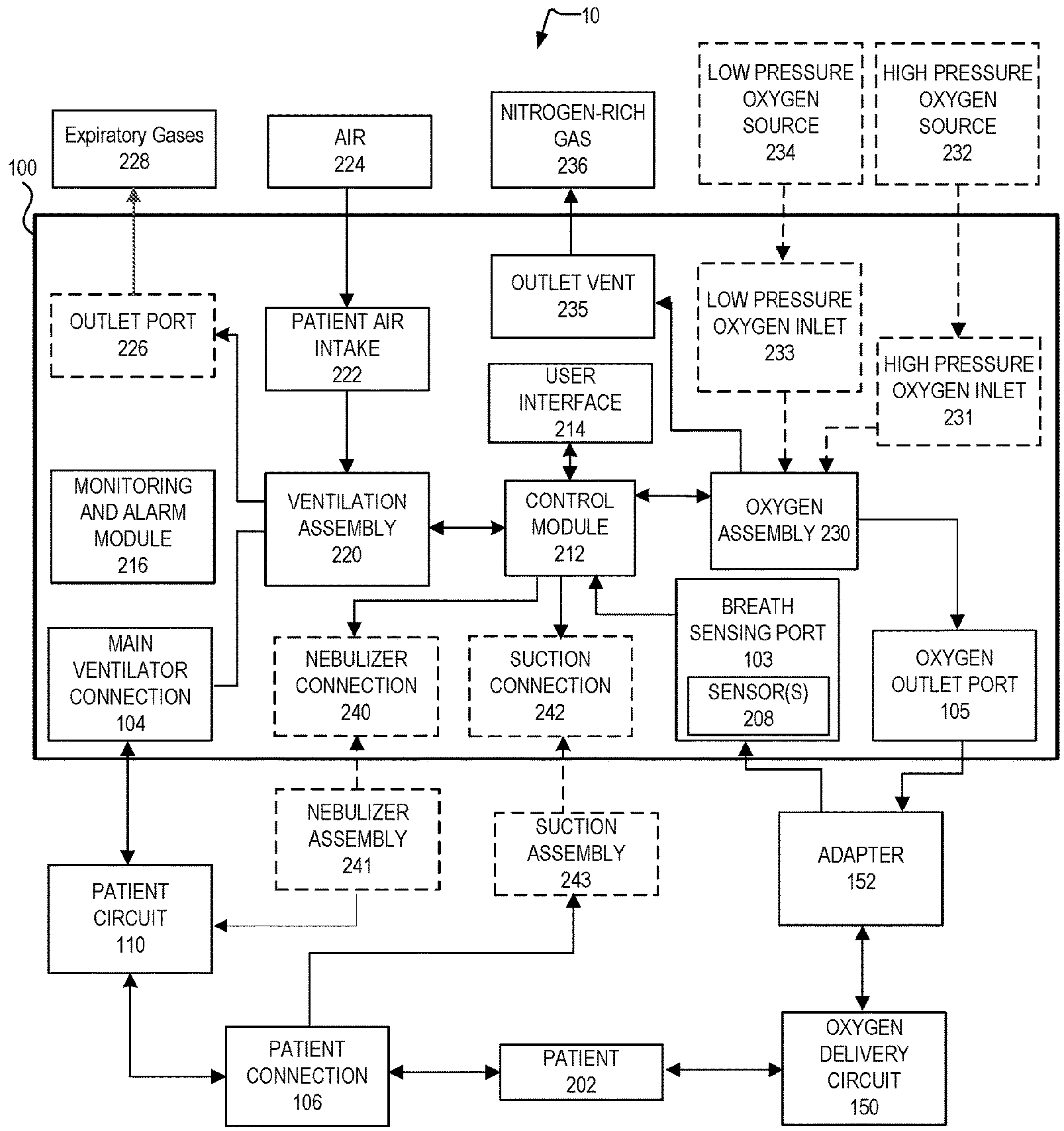
FIG. 2 is a schematic diagram of the ventilator system shown in FIGS. 1A-1C.

FIG. 2, which is a block diagram of the system 10, illustrates additional features of the system 10. As illustrated, the ventilator 100 can include a ventilation assembly 220 for providing ventilation or inspiratory gases (e.g., "air 224") to a patient 202. The air 224 is received by the ventilator 100 via a patient air intake 222, which is coupled to the ventilation assembly 220. While identified as being "air," those of ordinary skill in the art appreciate that the air 224 may include ambient air or pressurized air obtained from any source external to the ventilator 100. The ventilation assembly 220 can provide the air 224 to the main ventilator connection 104 during an inspiratory phase of a breath. In some embodiments, the ventilator 100 may receive expiratory gases during an expiratory phase of a breath. The ventilator may therefore have an outlet port 226 coupled to the ventilation assembly 220 for venting patient expiratory gases 228.

The ventilator 100 can be coupled to the patient 202 via the patient circuit 110 and the patient connection 106. The patient circuit 110, which can also be referred to herein as a "ventilation gas delivery circuit," can include a conduit or lumen (e.g., tubing) for transporting gases (e.g., the air 224 during the inspiratory phase and patient exhalation gases during an expiratory phase) to and/or from the patient 202. The patient circuit 110 can include a passive patient circuit or an active patient circuit, such as those described in U.S. Pat. Nos. 10,518,059 and 10,105,509, the disclosures of which are incorporated by reference herein in their entireties and for all purposes. The patient connection 106 can be any suitable interface coupled to the patient circuit 110 for delivering the air 224 to the patient 202, such as a full rebreather mask, a partial rebreather mask, a nasal mask, a mouthpiece, a tracheal tube, or the like.

The ventilator 100 can also include an oxygen assembly 230 for providing oxygen to the patient 202 via the oxygen outlet port 105. The oxygen can be generated internally within the ventilator, such as by a pressure-swing adsorption oxygen generator, including those described in U.S. Pat. No. 10,046,134, the disclosure of which is incorporated by reference herein in its entirety and for all purposes. When the oxygen is generated internally, the ventilator 100 may output exhaust gases (e.g., nitrogen-rich gas 236) via an outlet vent 235. In some embodiments, the oxygen may also be received from an optional low-pressure oxygen source 234 (e.g., an oxygen concentrator), and/or an optional high-pressure oxygen source 232. The ventilator 100 may therefore include a low-pressure oxygen inlet 233 configured to be coupled to the optional low-pressure oxygen source 234 and receive optional low-pressure oxygen therefrom. The ventilator 100 may also include an optional high-pressure oxygen inlet 231 configured to be coupled to the optional high-pressure oxygen source 232 and receive optional high-pressure oxygen therefrom.

The oxygen assembly 230 can be used by itself or in combination with the ventilation assembly 220 (e.g., to provide inspiratory gases mixed with oxygen). For example, the ventilator 100 can deliver pulses of oxygen to the oxygen delivery circuit 150, and the oxygen delivery circuit 150 can deliver the pulses of oxygen directly to the patient 202 (e.g., without mixing with the air 224 before being delivered to the patient). In other embodiments, a portion of the patient circuit 110 (e.g., the oxygen lumen 109 shown in FIG. 1C) can be coupled to the oxygen outlet port 105 such that the patient circuit 110 is coupled to both the main ventilator connection 104 and the oxygen outlet port 105, and oxygen can be mixed with the air 224 before being delivered to the patient, such as described in U.S. Pat. Nos. 10,245,406 and 10,315,002, previously incorporated by reference herein.

The ventilator 100 may include a control module 212 for controlling operation of the ventilator 100. For example, the control module 212 can generate one or more signals for controlling operation of the ventilation assembly 220 and/or the oxygen assembly 230. For example, the control module 212 can transition the ventilator 100 between the ventilation mode, the oxygen mode, and/or the combination mode. This may be done automatically or in response to a user input. The control module 212 can also synchronize operation of the ventilator 100 with the patient's breath. For example, in some embodiments, the control module 212 receives one or more measured parameters from the sensor(s) 208 at the breath sensing port 103. The ventilator 100 may therefore be configured to provide volume-controlled ventilation, pressure-controlled ventilation, and/or flow-controlled ventilation. For example, the control module 212 can analyze the measured parameter(s) received from the breath sensing port 103 and, based on the analysis, trigger delivery of a breath via the patient circuit 110 and/or trigger delivery of a pulse of oxygen via the oxygen delivery circuit 150. The control module 212 may also receive feedback signals from the ventilation assembly 220 and/or the oxygen assembly 230 to monitor and/or control the various aspects of the ventilator 100.

The ventilator 100 can further include a user interface 214. The user interface 214 is configured to receive input from a user (e.g., a caregiver, a clinician, or the like associated with the patient 202) and provide that input to the control module 212. The input received via the user interface 214 can include ventilator settings, parameters of operation, modes of operation, and the like. In a particular example, a user may select between the ventilation mode, the oxygen mode, and/or the combination mode using the user interface 214. The user interface 214 can further be configured to display information to the user and/or patient, including selected ventilator settings, parameters of operation, modes of operation, and the like. The user interface 214 can be any suitable user interface known in the art, such as a touch-screen having a digital display of ventilator settings and operating parameters.

The ventilator 100 can optionally include additional functions beyond the ventilation and oxygen delivery described herein. For example, the ventilator 100 can optionally include a nebulizer connection 240 for coupling to a nebulizer assembly 240 and/or a suction connection 242 for coupling to a suction assembly 243. The ventilator 100 may further include a cough-assist module (not shown) for providing cough assistance to the patient. The cough-assist module can be integrated with the ventilator 100 such that the system 10 can provide cough-assistance to the patient without disconnecting the patient from the patient circuit 110, as described in U.S. Pat. No. 9,956,371, the disclosure of which is incorporated by reference herein in its entirety and for all purposes. The ventilator 100 may further include a monitoring and alarm module 216.

Figure 3:
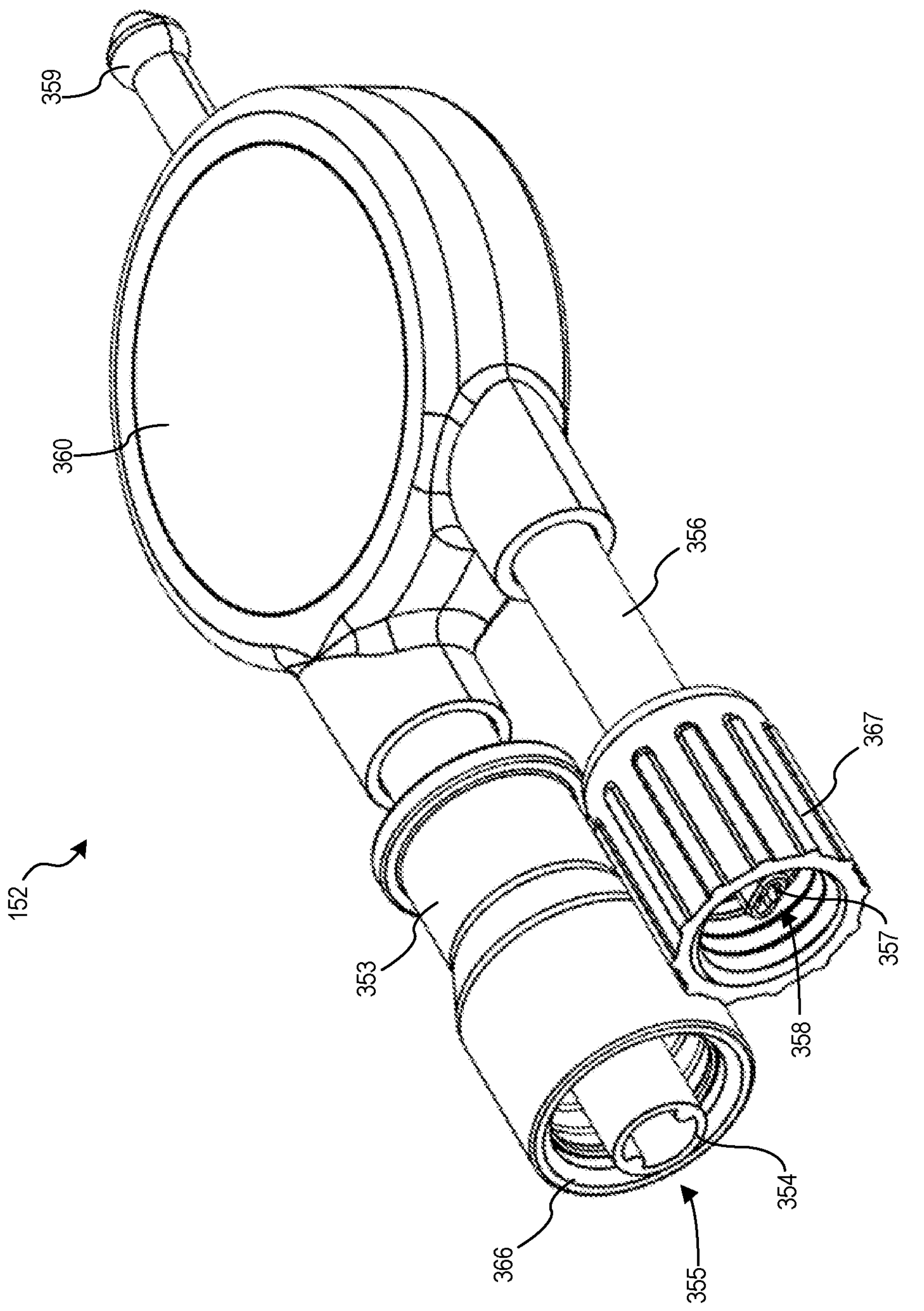
FIG. 3 is an isometric view of an adapter for use with a ventilator system and configured in accordance with embodiments of the present technology.

FIG. 3 is an enlarged isometric view of the adapter 152. The adapter 152 includes a first arm 353 extending between a body portion 360 of the adapter and an oxygen inlet port 354. The oxygen inlet port 354 can be connected to the oxygen outlet port 105 of the ventilator 100 for receiving oxygen therefrom. For example, the first arm 353 can include a first connection feature 366 for securing the adapter 152 to the oxygen outlet port 105. An oxygen lumen or conduit 355 can extend through the first arm 353 between the oxygen inlet port 354 and the body portion 360 for directing oxygen received at the oxygen inlet port 354 into the body portion 360 of the adapter 152. The adapter 152 further includes an oxygen delivery circuit connection feature 359 (also referred to herein as a "cannula connection feature") configured to releasably engage an oxygen delivery circuit, such the cannula shown in FIGS. 1 and 2. When an oxygen delivery circuit is connected to the adapter 152 at the oxygen delivery connection feature 359, oxygen flowing into the adapter 152 via the oxygen inlet port 354 flows out of the adapter 152 and into the oxygen delivery circuit via the oxygen delivery circuit connection feature 359.

The adapter 152 further includes a second arm 356 extending between the body portion 360 and a sensor connection port 357. The sensor connection port 357 can be connected to the breath sensing port 103 of the ventilator 100. For example, the second arm 356 can include a second connection feature 367 for securing the adapter 152 to the breath sensing port 103. A sensing lumen 358 can extend through the second arm 356 for providing parameters (e.g., pressure) associated with the patient's breathing to the breath sensing port 103 of the ventilator. As described in detail below, the adapter 152 prevents or at least reduces oxygen flowing from the oxygen inlet port 354 to the oxygen delivery circuit connection feature 359 from entering the sensing lumen 358, yet permits pressure signals induced by the patient's inspiratory efforts to be transmitted via the sensing lumen 358 to the breath sensing port 103 for triggering synchronized oxygen delivery.

Figure 4:
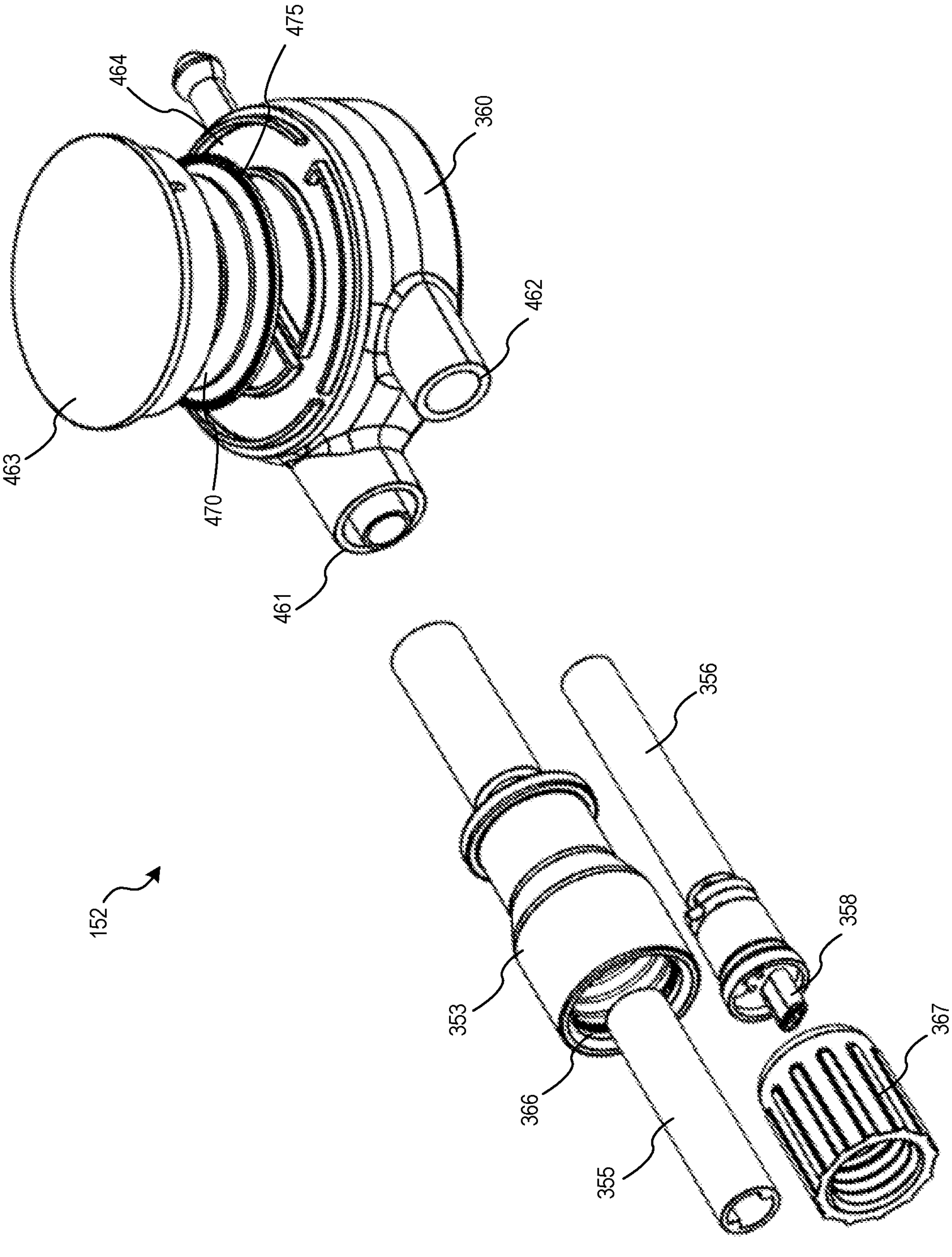
FIG. 4 is a partially exploded view of the adapter shown in FIG. 3.

FIG. 4 is an exploded view of the adapter 152. As illustrated, the body portion 360 can include a first port 461 and a second port 462. The first port 461 can be coupled to the first arm 353 such that it is in fluid communication with the oxygen lumen 355. The second port 462 can be coupled to the second arm 356 such that is in fluid communication with the sensing lumen 358. Although the first and second arms 353, 356 are shown as discrete components, in some embodiments one or both of the first and second arms 353, 356 may be integral with the body portion 360. The body portion 360 includes a cap portion 463 and a base portion 464. A diaphragm or membrane 470 and a stopper 475 are positioned between the cap portion 463 and the base portion 464. Additional details of the diaphragm 470 and the stopper 475 are described below with respect to FIGS. 5A and 5B.

Figure 5A:
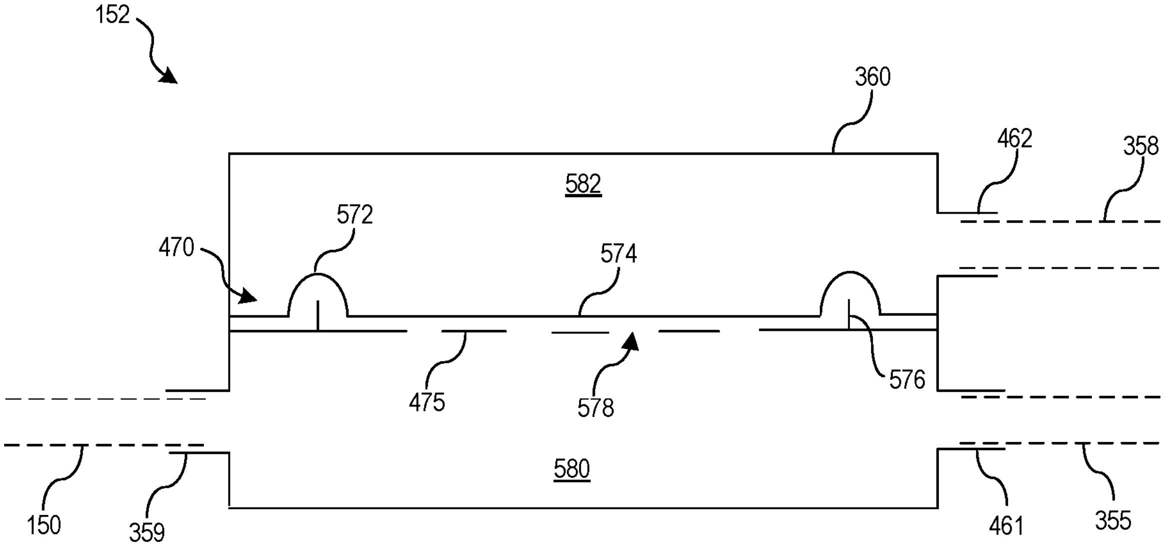
FIGS. 5A and 5B are schematic diagrams of various embodiments of the adapter shown in FIG. 3.

FIG. 5A is a schematic illustration of select aspects of the adapter 152. As illustrated, the diaphragm 470 is positioned within the body portion 360 and divides the body portion 360 into a first (e.g., lower) chamber 580 and a second (e.g., upper) chamber 582. The first chamber 580 is in fluid communication with the oxygen lumen 355 (via the first port 461) and the oxygen delivery circuit 150 (via the oxygen delivery circuit connection feature 359). The second chamber 582 is in fluid communication with the sensing lumen 358 (via the second port 462). The diaphragm 470 includes a raised portion or ridge 572 extending circumferentially around a central pressure transmitting membrane 574. The diaphragm 470 can be composed of a substantially gas-impermeable and semi-flexible material, such as rubber, silicone, or the like. Accordingly, the diaphragm 470 generally prevents fluid or gas from flowing between the first chamber 580 and the second chamber 582, yet facilitates a pressure change in the first chamber 580 to be at least partially transmitted across the pressure transmitting membrane 574 and into the second chamber 582.

The stopper 475 is also positioned within the body portion 360 adjacent the diaphragm 470. For example, in embodiment illustrated in FIG. 5A, the stopper 475 is positioned in the first chamber 580 (e.g., between the diaphragm 470 and the oxygen lumen 355). The stopper 475 includes a plurality of openings 578 that permit the pressure transmitting membrane 574 to perceive at least a fraction of a pressure change within the first chamber 580. The stopper 475 also includes one or more ridge-like projections corresponding to the raised portion 572 of the diaphragm 470. Without being bound by theory, the stopper 475 is expected to reduce or prevent the diaphragm 470 from inverting, e.g., when the pressure within the first chamber 580 is significantly less than the pressure within the second chamber 582.

During operation (e.g., when the system 10 (FIG. 1) is being used to deliver oxygen to a patient via an oxygen delivery circuit such as a cannula), a patient's initial inspiratory effort may induce a negative pressure in the oxygen delivery circuit 150 and the first chamber 580. The stopper 475 prevents the diaphragm 470 from inverting from the negative pressure in the first chamber 580. However, the negative pressure induced by the patient's inspiratory effort is at least partially transmitted to the second chamber 582 through the pressure transducing membrane 574. The negative pressure is then transmitted from the second chamber 582 to the breath sensing port 103 (FIG. 2) of the ventilator 100 via the sensing lumen 358. As a result, the negative pressure induced by the patient's inspiratory efforts can be measured by the breath sensing port 103 and used to trigger delivery of a pulse of oxygen during a patient's inspiratory phase. In some embodiments, the diaphragm allows 100% pressure transmission between the first chamber and the second chamber (e.g., the pressure in the first chamber 580 is equal to the pressure in the second chamber 582 during the patient's initial inspiratory effort). In other embodiments, the diaphragm allows less than 100% pressure transmission (e.g., about 90%, about 80%, about 70%, about 60%, about 50%, etc.) from the first chamber 580 to the second chamber 582, yet sufficient pressure transmission to indicate the onset of the patient's breath and trigger delivery of the pulse of oxygen. For example, in some embodiments the diaphragm 470 may transmit at least 50% of the patient signal to the sensing lumen 358.

Once the pulse of oxygen is triggered, the ventilator 100 delivers oxygen to the patient via the oxygen delivery circuit 150. Because the adapter 152 is positioned between the oxygen delivery circuit 150 and the ventilator 100, the oxygen flows through the adapter 152. More specifically, the oxygen travels through the oxygen lumen 355, into the first chamber 580, and into the oxygen delivery circuit 150 at the oxygen delivery circuit connection feature 359. In some embodiments, such as described with respect to FIGS. 6A-7B, the adapter 152 can include another flow path for oxygen to travel through as it moves from the oxygen lumen 355 to the oxygen delivery circuit 150 that at least partially bypasses the first chamber 580 to reduce the effects of the oxygen on the diaphragm 470. Regardless of whether there is a bypass, and as previously described, the diaphragm 470 prevents the oxygen from flowing from the first chamber 580 to the second chamber 582. This is expected to provide several advantages. First, it conserves oxygen by directing oxygen to flow into the oxygen delivery circuit 150 instead of into the second chamber 582, and thus to the patient. Second, it prevents the pressure within the second chamber 582 and the sensing lumen 358 from raising above a threshold value that may damage the sensors 208 and/or the breath sensing port 103 on the ventilator 100. For example, the diaphragm 470 may prevent the pressure within the sensing lumen 358 and/or at the breath sensing port 103 from exceeding about 5 PSI, about 6 PSI, about 7 PSI, about 8 PSI, about 9 PSI, and/or about 10 PSI during delivery of the oxygen pulse. Third, the diaphragm 470 provides a physical barrier to protect the sensors 208 and the breath sensing port 103 from environmental conditions, such as condensation or dust.

Figure 5B:
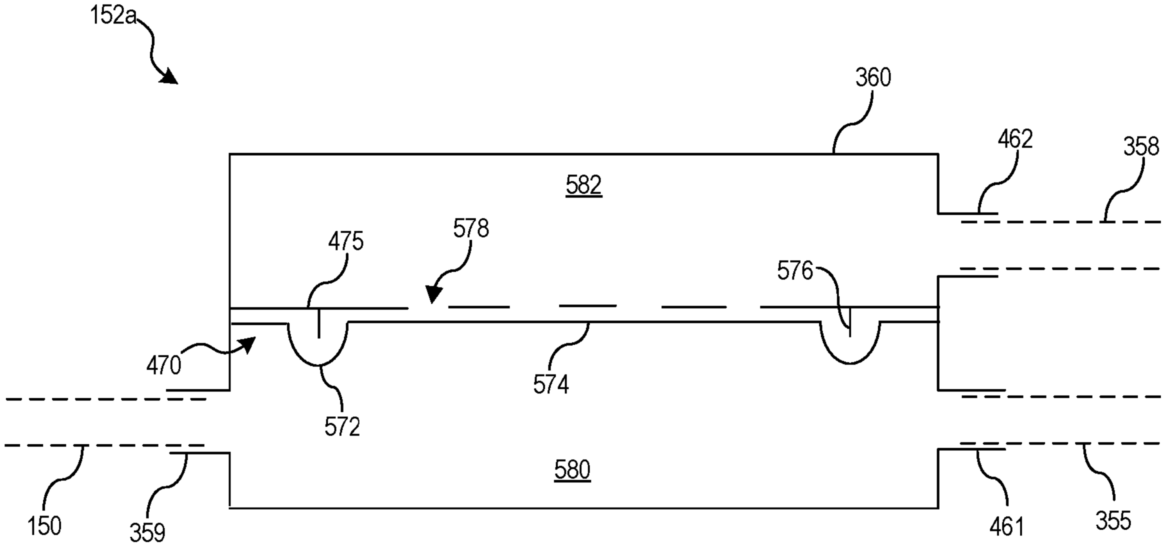

FIG. 5B illustrates another embodiment of an adapter 152*a* configured in accordance with embodiments of the present technology. The adapter 152*a* is generally similar to the adapter 152 described with respect to FIG. 5A, except the stopper 475 is positioned in the second chamber 582 (e.g., between the diaphragm 470 and the sensing lumen 358) instead of the first chamber 580 and the orientation of the diaphragm 470 is flipped. As a result, the stopper 475 prevents the diaphragm 470 from inverting as oxygen is being delivered to the patient. Without being bound by theory, placing the stopper in the second chamber 582 may also further reduce the pressure generated in the second chamber 582 during oxygen delivery, and thus the pressure at the breath sensing port 103 during oxygen delivery, by reducing the distance to which the diaphragm 470 can deflect into the second chamber 582. However, the diaphragm can still deflect into the first chamber 580 in response to a negative pressure generated by a patient's inspiratory effort to transmit a negative pressure into the second chamber 582 to trigger delivery of a pulse of oxygen. In some embodiments, the adapters described herein can have a stopper 475 in both the first chamber 580 and the second chamber 582.

Figure 6A:
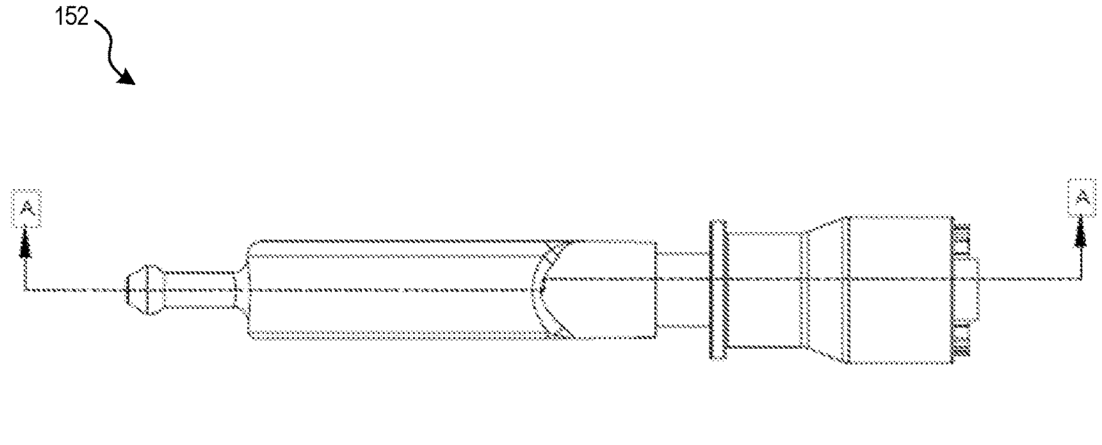
FIG. 6A is a side view of the adapter shown in FIG. 3.
Figure 6B:
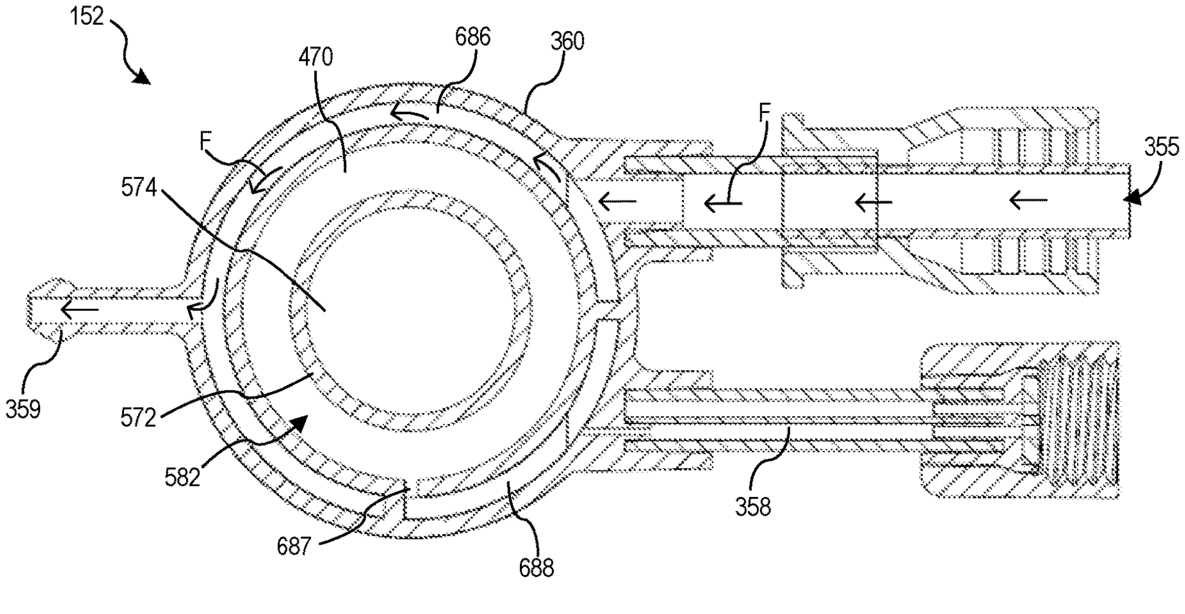
FIG. 6B is a cross-section of the adapter taken along the axis indicated in FIG. 6A.
Figure 7A:
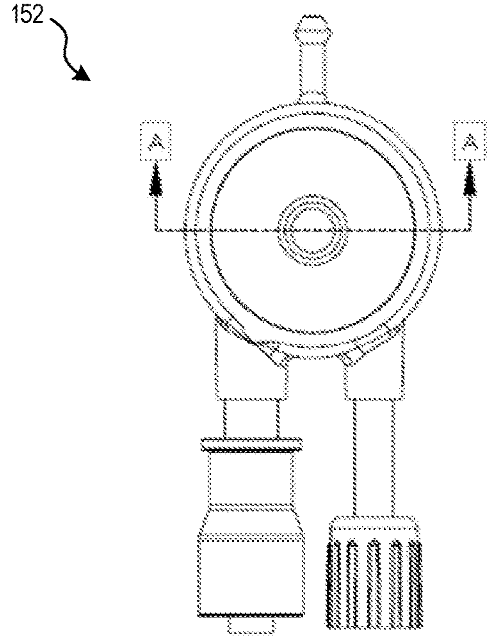
FIG. 7A is a top view of the adapter shown in FIG. 3.
Figure 7B:
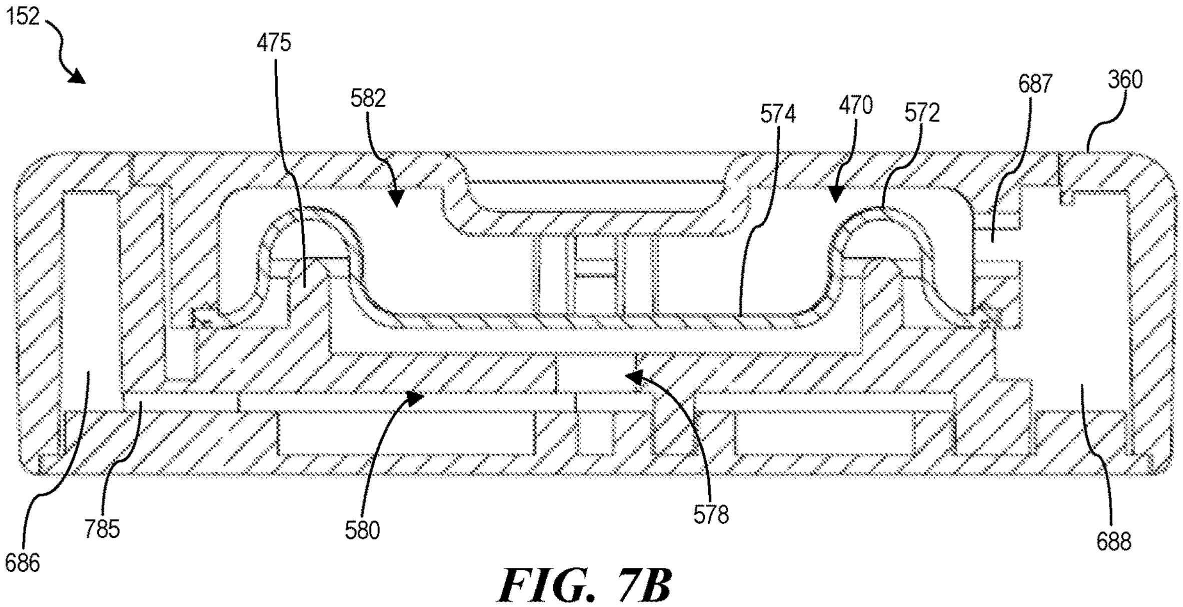
FIG. 7B is a cross-section of the adapter taken along the axis indicated in FIG. 7A.

FIG. 6A is a side view of the adapter 152, and FIG. 6B is a cross-section view of the adapter 152 taken along the axis A-A indicated in FIG. 6A. FIG. 7A is a top view of the adapter 152, and FIG. 7B is a cross-section view of the adapter 152 taken along the axis A-A indicated in FIG. 7B. Referring first to FIG. 6B, the body portion 360 includes a first conduit 686 fluidly coupled to the oxygen lumen 355 and the oxygen delivery circuit connection feature 359. During operation, oxygen flows from the oxygen lumen 355 to the oxygen delivery circuit connection feature 359 via the first conduit 686, as indicated by the arrows F. The first conduit 686 generally bypasses the first chamber 580 (not shown in FIG. 6B) and the second chamber 582 to reduce the interaction of the oxygen flow with the diaphragm 470. However, as best shown in FIG. 7B, a channel 785 fluidly connects the first conduit 686 with the first chamber 580 such that negative pressure induced by the patient's initial inspiratory effort is still sensed at the diaphragm 470. Referring now to both FIG. 6B and FIG. 7B, the body portion 360 also includes a second conduit 688 fluidly coupled to the second chamber 582 via an inlet 687. The second conduit 688 fluidly couples the second chamber 582 to the sensing lumen 358. Accordingly, negative pressure generated by the patient's initial inspiratory efforts in the second chamber 582 is transmitted to the sensing lumen 358 via the inlet 687 and the second conduit 688.

The adapter 152 may take other forms beyond those explicitly shown herein. In some embodiments, for example, the adapter 152 may include multiple diaphragms and/or pressure transmitting membranes. The adapter 152 can also include an expandable member (e.g., a balloon) in addition to, or in lieu of, the diaphragm 470. The expandable balloon can be made of a compliant/elastic material configured to transmit at least a portion of a negative pressure induced in the oxygen delivery circuit during a patient's initial inspiratory effort to the sensor for triggering the delivery of the pulse of oxygen and/or the breath while also preventing a pressure at the sensor from exceeding a maximum threshold value during delivery of the pulse of oxygen. The expandable balloon can therefore also be described as a pressure transmitting membrane. Further yet, the adapter 152 may include a pressure relief valve to prevent the pressure at the sensor from exceeding a maximum threshold value during delivery of the pulse of oxygen.

Figure 8:
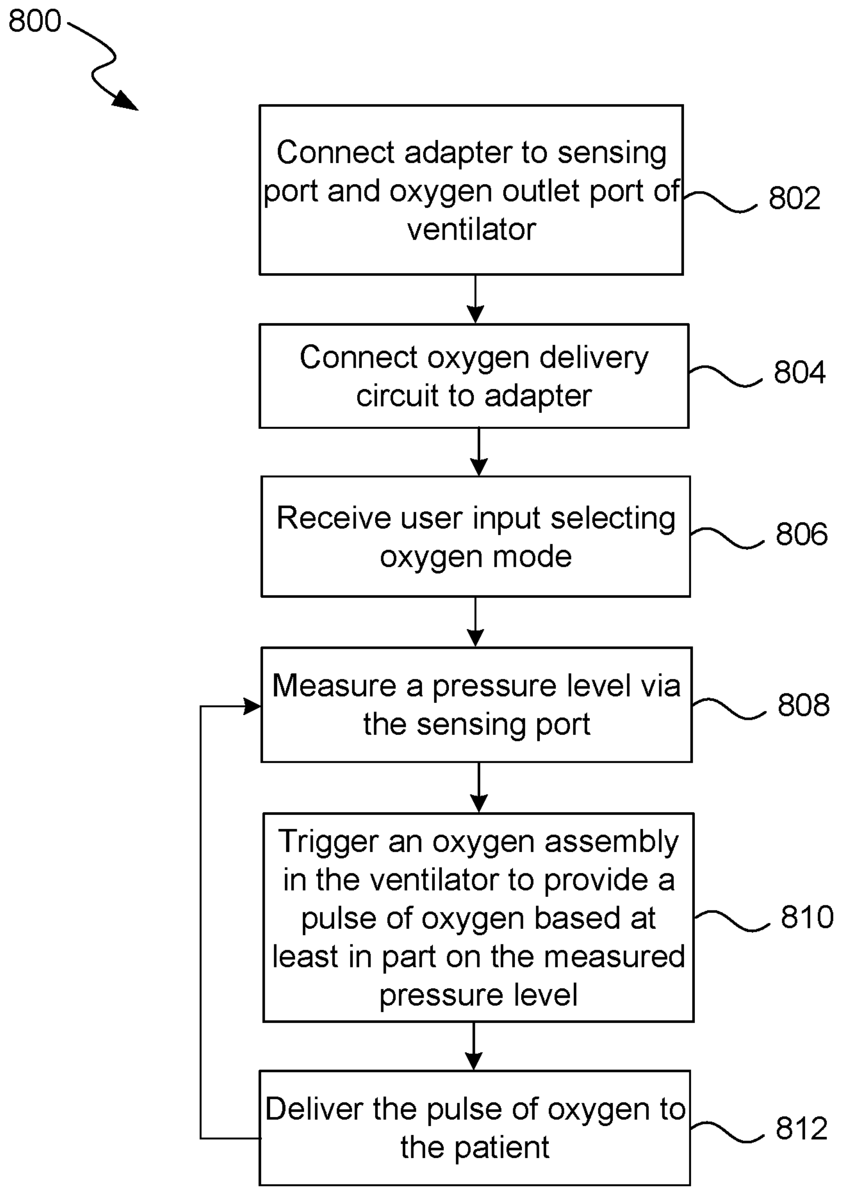
FIG. 8 is a flowchart of a method for providing oxygen therapy to a patient in accordance with embodiments of the present technology.

The present technology further provides methods for delivering therapy to a patient. For example, FIG. 8 is a flowchart of a method 800 for providing oxygen therapy to a patient using a ventilator, such as the ventilator 100 described herein. The method 800 can begin in step 802 by connecting an adapter to a sensing port and an oxygen outlet port of the ventilator. In some embodiments, the adapter can be generally similar to or the same as the adapter 152 described herein. Accordingly, connecting the adapter to the sensing port can include placing a sensing lumen within the adapter in fluid communication with the sensing port, and connecting the adapter to the oxygen outlet port can include placing an oxygen lumen within the adapter in fluid communication with the oxygen outlet port. The method 800 can continue in step 802 by connecting an oxygen delivery circuit to the adapter. The oxygen delivery circuit can be a conventional nasal cannula, as previously described, and can be connected to the adapter through any suitable means known in the art (e.g., via a friction fit). In some embodiments, the adapter can be integrally manufactured with the oxygen delivery circuit, such that step 804 is omitted. The oxygen delivery circuit can also be connected to the patient.

The method 800 can continue in step 806 by receiving, via a user interface on the ventilator, a user input corresponding to a selection of an "oxygen mode." For example, in some embodiments the ventilator may include a touch-screen display, and a user can select "oxygen mode" from a menu of therapy options. In response to the receiving the user input in step 806, a control assembly within the ventilation can initiate oxygen mode, during which the ventilator delivers pulses of oxygen to a patient. In some embodiments, step 806 can occur before steps 802 and 804.

With the ventilator operating in oxygen mode, the method 800 continues in step 808 by measuring a pressure level via the sensing port. For example, the sensing port may measure a pressure level corresponding to a pressure within the oxygen delivery circuit that is transmitted to the sensing port via the adapter, as previously described herein. The method 800 continues in step 810 by triggering an oxygen assembly in the ventilator to provide a pulse of oxygen based at least in part on the measured pressure level. For example, the oxygen assembly can be triggered when the measured pressure level crosses a predetermined threshold, such as a threshold corresponding to a patient's initial inspiratory efforts, such that delivery of the oxygen pulse coincides with a patient's natural inspiration. In some embodiments, the predetermined threshold is 0 PSI, and the oxygen assembly is triggered when the pressure in the system transitions from positive to negative (indicating the patient has begun inspiration). In another embodiment, the predetermined threshold is a non-zero value corresponding to a baseline pressure value in the system, and the oxygen assembly is triggered when the pressure in the system falls below the baseline pressure value in the system. In another embodiment, the predetermined threshold is a rate of change of the pressure value of the system.

Once the oxygen assembly is triggered, the method 800 continues in step 812 by delivering the pulse of oxygen to the patient. This can include, for example, routing the pulse of oxygen from the ventilator, through the adapter coupled to the oxygen outlet port of the ventilator, and into the oxygen delivery circuit for delivery to the patient. As described previously, the adapter can prevent the pressure level at the sensing port from exceeding a maximum threshold value (e.g., 5 PSI, 10 PSI, etc.) during delivery of the pulse of oxygen. The method 800 can continue by iteratively repeating steps 808, 810, and 812 to provide pulses of oxygen to a patient synchronized with the patient's respiration.

Figure 9:
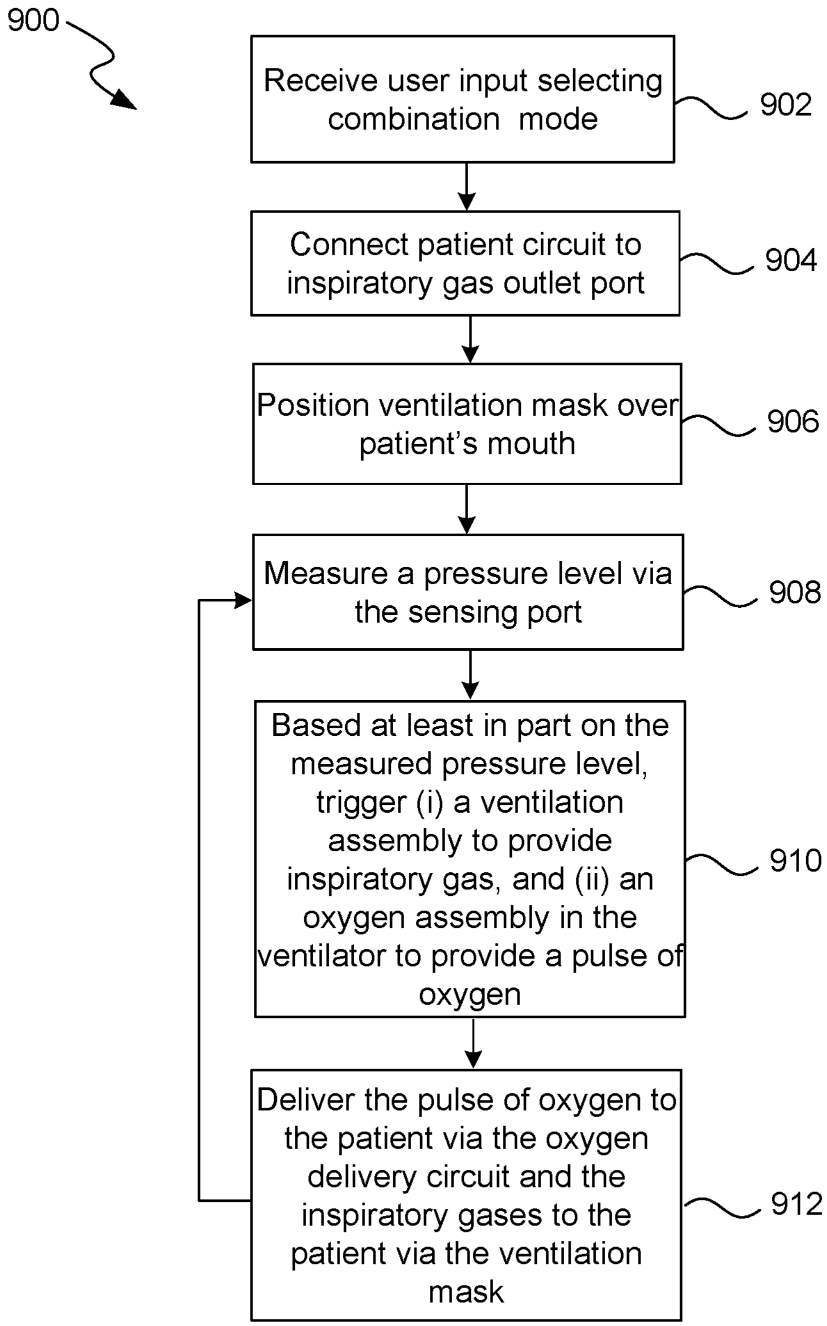
FIG. 9 is a flowchart of a method for providing oxygen therapy and ventilation therapy to a patient in accordance with embodiments of the present technology.

FIG. 9 is a flowchart of a method 900 for providing oxygen therapy and ventilation therapy to a patient using a ventilator in accordance with embodiments of the present technology. The method 900 can begin in step 902 by receiving, via a user interface on the ventilator, a user input corresponding to a selection of a "combination mode," which includes both ventilation therapy and oxygen therapy. For example, in some embodiments the ventilator may include a touch-screen display, and a user can select "combination mode" from a menu of therapy options. In some embodiments, the user input is received while the ventilator is already operating in oxygen mode to deliver pulses of oxygen to the patient, as described with respect to FIG. 8. Accordingly, step 902 can occur at any point during the iterative process of steps 808, 810, and 812 described with respect to FIG. 8. The following description of the method 900 will be directed to such embodiments in which the ventilator is already operating in oxygen mode when the user selects combination mode. However, as one skilled in the art will appreciate from the disclosure herein, the user input in step 902 can also be received while the ventilator is operating in ventilation mode or is neither operating in ventilation mode or oxygen mode.

The method 900 can continue in step 904 by connecting a first end portion of a patient circuit (e.g., the patient circuit 110) to an inspiratory gas outlet port (e.g., the main ventilator connection 104 of the ventilator 100). The patient circuit can be any suitable patient circuit known in the art for delivering ventilation therapy to a patient, such as an elongated corrugated conduit. The method 900 can continue in step 906 by positioning a ventilation mask coupled to a second end portion of the patient circuit over the patient's mouth and/or nose. If the patient is already receiving oxygen therapy, positioning the ventilation mask over the patient's mouth and/or nose can include positioning the ventilation mask over the oxygen delivery circuit (e.g., the nasal cannula) that is delivering the oxygen to the patient.

With the ventilator operating in combination mode, the method 900 continues in step 908 by measuring a pressure level via the sensing port. For example, the sensing port may continue to measure a pressure level corresponding to a pressure within the oxygen delivery circuit that is transmitted to the sensing port via an adapter, as described with respect to FIG. 8. The method 900 continues in step 910 by triggering (1) the oxygen assembly in the ventilator to provide a pulse of oxygen, and (2) a ventilation assembly in the ventilator to provide inspiratory gases (e.g., air) based at least in part on the measured pressure level. For example, the oxygen assembly and the ventilation assembly can be triggered when the measured pressure level crosses a predetermined threshold, such as a threshold corresponding to a patient's initial inspiratory efforts, such that delivery of the oxygen pulse and the inspiratory gases coincides with a patient's natural inspiration.

Once the ventilation assembly and the oxygen assembly are triggered, the method 900 continues in step 912 by delivering the pulse of oxygen and the inspiratory gases to the patient. As described above with respect to the method 800, the pulse of oxygen can be routed from the ventilator, through the adapter coupled to the oxygen outlet port of the ventilator, and into the oxygen delivery circuit for delivery to the patient. The inspiratory gases can be routed from the ventilator, through the patient circuit, and into the ventilation mask for delivery to the patient. In some embodiments, the pulse of oxygen and the inspiratory gases are delivered to the patient simultaneously. In other embodiments, the pulse of oxygen is delivered first, and the inspiratory gases are delivered at or after the delivery of the pulse is terminated. However, even when the delivery of the oxygen and inspiratory gases is offset, the inspiratory gases are still delivered during the patient's natural inspiratory phase. Moreover, although described as providing inspiratory gases during a patient's natural inspiratory phase, one skilled in the art will appreciate that the method 900 can also include providing a positive pressure within the patient circuit throughout the patient's breathing cycles (e.g., during both the patient's inspiratory and expiratory phases), consistent with positive-end-expiratory-pressure (PEEP) ventilation. The method 900 can continue by iteratively repeating steps 908, 910, and 912 to provide pulses of oxygen and inspiratory gases to a patient synchronized with the patient's respiration.

As one of skill in the art will appreciate from the disclosure herein, various components of the systems described above can be omitted without deviating from the scope of the present technology. For example, in some embodiments the adapter can be omitted, and the oxygen delivery circuit (e.g., the cannula) can have a first lumen extending between the breath sensing port 103 and the patient and a second lumen extending between the oxygen outlet port 105 and the patient. The first lumen can be used to sense the patient's initiation of inspiration, and the second lumen can be used to deliver pulses of oxygen to the patient. The first and second lumens can be fluidly isolated to ensure that the breath sensing port 103 remains fluidly isolated from the oxygen outlet port 105 during application of oxygen pulses.

Likewise, additional components not explicitly described above may be added to the systems without deviating from the scope of the present technology. For example, it will be appreciated that specific embodiments of the technology have been described herein for purposes of illustration, but well-known structures and functions have not been shown or described in detail to avoid unnecessarily obscuring the description of the embodiments of the technology. Moreover, although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. Accordingly, the present technology is not limited to the configurations expressly identified herein, but rather encompasses variations and alterations of the described systems and methods.

Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Further, where specific integers are mentioned herein which have known equivalents in the art to which the embodiments relate, such known equivalents are deemed to be incorporated herein as if individually set forth.

We claim:

1. A ventilator system for providing therapy to a patient, comprising:

a housing;

a ventilation assembly in the housing and configured to provide a breath composed at least partially of inspiratory gas, the ventilation assembly including a ventilation port in the housing for providing the inspiratory gas to a patient circuit;

an oxygen assembly in the housing and having an oxygen source configured to provide oxygen, the oxygen assembly further including an oxygen port in the housing for delivering the oxygen to an oxygen delivery circuit;

a sensor configured to measure a pressure level for triggering delivery of the breath and/or the oxygen; and an adapter configured to interface with the oxygen port, the oxygen delivery circuit, and the sensor, wherein the adapter is further configured to (i) transmit at least a portion of a reduction in pressure induced in the oxygen delivery circuit during a patient's initial inspiratory effort to the sensor for triggering the delivery of the oxygen and/or the breath, and (ii) route the oxygen from the oxygen outlet port to the oxygen delivery circuit, wherein the system is transitionable between (a) a ventilation mode in which the ventilation assembly provides inspiratory gas to the patient circuit, (b) an oxygen mode in which the oxygen assembly provides oxygen to the oxygen delivery circuit, and (c) a combination mode in which the ventilation assembly provides inspiratory gas to the patient circuit and the oxygen assembly provides oxygen to the oxygen delivery circuit.

2. The ventilator system of claim 1, further comprising a control module configured to transition the system between the ventilation mode, the oxygen mode, and/or the combination mode.

3. The ventilator system of claim 2 wherein the control module is configured to automatically transition the system between the ventilation mode, the oxygen mode, and/or the combination mode.

4. The ventilator system of claim 2 wherein the control module is configured to transition the system between the ventilation mode, the oxygen mode, and/or the combination mode in response to a user input.

5. The ventilator system of claim 1 wherein the patient circuit is distinct from the oxygen delivery circuit.

6. The ventilator system of claim 1 wherein the oxygen delivery circuit is a cannula.

7. The ventilator system of claim 1, further comprising the oxygen delivery circuit, and wherein the oxygen delivery circuit includes:

a first lumen configured to extend between a sensor port housing the sensor and the patient, and a second lumen configured to extend between the oxygen port and the patient, wherein the first lumen and the second lumen are fluidly isolated.

8. The ventilator system of claim 1 wherein the oxygen includes one or more pulses of oxygen.

9. A ventilator system for providing therapy to a patient, comprising:

a ventilation assembly configured to provide a breath composed at least partially of inspiratory gas, the ventilation assembly including a ventilation port for providing the inspiratory gas to a patient circuit;

an oxygen assembly configured to provide oxygen, the oxygen assembly including an oxygen port for delivering the oxygen to an oxygen delivery circuit;

a sensor configured to measure a pressure level for triggering delivery of the breath and/or the oxygen; and an adapter configured to interface with the oxygen port, the oxygen delivery circuit, and the sensor, wherein the adapter is further configured to (i) transmit at least a portion of a reduction in pressure induced in the oxygen delivery circuit during a patient's initial inspiratory effort to the sensor for triggering the delivery of the oxygen and/or the breath and (ii) route the oxygen from the oxygen outlet port to the oxygen delivery circuit, wherein the system is transitionable between (a) a ventilation mode in which the ventilation assembly provides inspiratory gas to the patient circuit, (b) an oxygen mode in which the oxygen assembly provides oxygen to the oxygen delivery circuit, and (c) a combination mode in which the ventilation assembly provides inspiratory gas to the patient circuit and the oxygen assembly provides oxygen to the oxygen delivery circuit.

10. The ventilator system of claim 9 wherein the adapter is further configured to (iii) prevent a pressure at the sensor from exceeding a maximum threshold value during delivery of the oxygen.

11. The ventilator system of claim 9 wherein the adapter includes a pressure-transmitting membrane.

12. The ventilator system of claim 9 wherein the adapter includes a pressure relief valve.

13. A method of treating a patient using a ventilator having an oxygen assembly, a ventilation assembly, and a sensor positioned within a common housing, the method comprising:

transmitting at least a portion of a reduction in pressure induced in an oxygen delivery circuit during the patient's initial inspiratory effort to the sensor via an adapter having a first portion coupled to the oxygen delivery circuit and a second portion coupled to the sensor;

in response to transmitting the at least portion of the reduction in pressure, operating the ventilator in an oxygen mode to provide a pulse of oxygen to the patient via the oxygen assembly, an oxygen outlet port in the common housing, and an oxygen delivery circuit, wherein a third portion of the adapter is coupled to the oxygen outlet port such that oxygen flows through the adapter between the oxygen outlet port and the oxygen delivery circuit, wherein in the oxygen mode the patient does not receive ventilation gases; and in response to a user input, operating the ventilator in a combination mode to provide (1) the oxygen to the patient via the oxygen assembly and the oxygen delivery circuit, and (2) ventilation gases to the patient via the ventilation assembly and a ventilation gas delivery circuit coupled to the ventilator, wherein the patient remains continuously connected to the oxygen delivery circuit and receives the oxygen during the transition from the oxygen mode to the combination mode.

14. The method of claim 13 wherein the ventilation gas delivery circuit includes a patient mask and the oxygen delivery circuit includes a cannula, the method further comprising positioning the patient mask over the cannula before operating the ventilator in the combination mode.

15. The method of claim 13 wherein the ventilator is portable.

16. The method of claim 13 wherein the oxygen is provided to the patient as one or more pulses of oxygen in both the oxygen mode and the combination mode.

* * * * *